US008298781B2

(12) United States Patent
Matsunami et al.

(10) Patent No.: US 8,298,781 B2
(45) Date of Patent: Oct. 30, 2012

(54) COMPOSITIONS AND METHODS FOR CHARACTERIZING AND REGULATING OLFACTORY SENSATION

(75) Inventors: Hiroaki Matsunami, Durham, NC (US); Andreas Keller, New York, NY (US); Hanyi Zhuang, Delray Beach, FL (US); Qiuyi Chi, Durham, NC (US); Leslie B. Vosshall, New York, NY (US)

(73) Assignees: Duke University, Durham, NC (US); The Rockefeller University, New York, NY (US)

( * ) Notice: Subject to any disclaimer, the term of this patent is extended or adjusted under 35 U.S.C. 154(b) by 0 days.

(21) Appl. No.: 12/598,901

(22) PCT Filed: May 8, 2008

(86) PCT No.: PCT/US2008/063073
§ 371 (c)(1),
(2), (4) Date: Jan. 21, 2010

(87) PCT Pub. No.: WO2008/137993
PCT Pub. Date: Nov. 13, 2008

(65) Prior Publication Data
US 2010/0143337 A1    Jun. 10, 2010

Related U.S. Application Data

(60) Provisional application No. 60/928,249, filed on May 8, 2007.

(51) Int. Cl.
*G01N 33/567* (2006.01)
*C07K 14/705* (2006.01)

(52) U.S. Cl. .................... 435/7.2; 435/7.31; 436/501

(58) Field of Classification Search .................. None
See application file for complete search history.

(56) References Cited

U.S. PATENT DOCUMENTS

| | | | |
|---|---|---|---|
| 5,096,815 | A | 3/1992 | Ladner et al. |
| 5,198,346 | A | 3/1993 | Ladner et al. |
| 5,223,409 | A | 6/1993 | Ladner et al. |
| 5,733,731 | A | 3/1998 | Schatz et al. |
| 5,811,238 | A | 9/1998 | Stemmer et al. |
| 5,830,721 | A | 11/1998 | Stemmer et al. |
| 5,837,458 | A | 11/1998 | Minshull et al. |
| 6,506,559 | B1 | 1/2003 | Fire et al. |
| 2006/0057640 | A1 | 3/2006 | Matsunami et al. |

FOREIGN PATENT DOCUMENTS

| | | |
|---|---|---|
| EP | 025949 | 7/1983 |
| EP | 1612222 | 1/2006 |
| WO | 95/21931 | 8/1995 |
| WO | 96/25508 | 8/1996 |
| WO | 01/27158 | 4/2001 |
| WO | 01/90187 | 11/2001 |

OTHER PUBLICATIONS

McClintock and Sammeta, 2003, "Trafficking prerogatives of olfactory receptors", Neuroreport, 14(12): 1547-1552.

McClintock et al., 1997, "Functional expression of olfactory-adrenergic receptor chimeras and intracellular retention of heterologously expressed olfactory receptors", Brain Res Mol Brain Res 48(2), 270-278.
McConnell et al., 1992, "The cytosensor microphysiometer: biological applications of silicon technology", Science, 257(5078): 1906-1912.
McLatchie et al., 1988, "RAMPs regulate the transport and ligand specificity of the calcitonin-receptor-like receptor", Nature, 393(6683): 333-339.
Menashe et al., 2003, "Different noses for different people", Nat Genet, 34(2): 143-144.
Miller et al., 1987, "N-terminal methionine-specific peptidase in *Salmonella typhimurium*", Proc Natl Acad Sci USA, 84:2718.
Milligan and Uhlenbeck, 1989, "Synthesis of small RNAs using T7 RNA polymerase", Methods in Enzymology, 180: 51-62.
Mombaerts, 1996, "Visualizing an olfactory sensory map", Cell, 87(4): 675-686.
Mombaerts, 1999, "Molecular biology of odorant receptors in vertebrates", Annu Rev Neurosci, 22: 487-509.
Mombaerts, 2004, "Genes and ligands for odorant, vomeronasal and taste receptors", Nat Rev Neurosci, 5(4): 263-278.
Moore and Arnold, 1996, "Directed evolution of a para-nitrobenzyl esterase for aqueous-organic solvents", Nat Biotechnol, 14(4): 458-467.
Narang, 1983, "DNA Synthesis", Tetrahedron Lett, 39:39.
Nardelli et al., 1992, "A chemically defined synthetic vaccine model for HIV-1", J. Immunol, 148(3):914-920.
Posnett et al., 1988, "A novel method for producing anti-peptide antibodies, Production of site-specific antibodies to the T cell antigen receptor beta-chain", J. Biol Chem,, 263(4): 1719-1725.
Raming et al., 1993, "Cloning and expression of odorant receptors", Nature, 361(6410): 353-356.
Roberge et al., 1995, "A strategy for a convergent synthesis of N-linked glycopeptides on a solid support", Science, 269(5221): 202-204.
Roberts et al., 1992, "Directed evolution of a protein: selection of potent neutrophil elastase inhibitors displayed on M13 fusion phage", Proc Natl Acad Sci USA, 89(6):2429-2433.
Saito et al., 2004, "RTP family members induce functional expression of mammalian odorant receptors", Cell, 119(5): 679-691.
Schlienger et al., 1992, "Human immunodeficiency virus type 1 major neutralizing determinant exposed on hepatitis B surface antigen particles is highly immunogenic in primates", J. Virol, 66(4):2570-2576.
Scott et al., 1990, "Searching for Peptide Ligands with an Epitope Library", Science, 249:386.

(Continued)

*Primary Examiner* — John Ulm
(74) *Attorney, Agent, or Firm* — Casimir Jones SC

(57) ABSTRACT

The present invention relates to the characterization of odorant receptors. In particular, the present invention relates to the OR7D4 proteins and nucleic acids encoding OR7D4 proteins and cell systems for screening for modulators of OR7D4 receptors. The present invention further provides assays for the detection of OR7D4 polymorphisms and mutations associated with altered olfactory sensation states, as well as methods of screening for therapeutic agents, ligands, and modulators of OR7D4 receptors.

11 Claims, 8 Drawing Sheets

OTHER PUBLICATIONS

Serizawa et al., 2003, "Negative feedback regulation ensures the one receptor-one olfactory neuron rule in mouse", Science, 302(5653): 2088-2094.
Shieh et al., 1989, "The ninaA gene required for visual transduction in Drosophila encodes a homologue of cyclosporin A-binding protein", Nature, 338(6210): 67-70.
Smith, 1994, "Applied evolution, the progeny of sexual PCR", Nature, 370(6488): 324-325.
Spehr et al., 2003, "Identification of a testicular odorant receptor mediating human sperm chemotaxis", Science, 299 (5615): 2054-2058.
Stemmer, 1994, "DNA shuffling by random fragmentation and reassembly: in vitro recombination for molecular evolution", Proc Natl Acad Sci USA, 91(22): 10747-10751.
Stemmer, 1994, "Rapid evolution of a protein in vitro by DNA shuffling", Nature, 370(6488): 389-391.
Touhara et al., 1999, "Functional identification and reconstitution of an odorant receptor in single olfactory neurons", Proc Natl Acad Sci USA, 96(7): 4040-4045.
Tuschl and Borkhardt, 2002, "Small interfering RNAs: a revolutionary tool for the analysis of gene function and gene therapy", Mol, Interv,, 2(3): 158-67.
Wahl et al., 1987, "Molecular hybridization of immobilized nucleic acids: theoretical concepts and practical considerations", Methods Enzymol 152: 399-407.
Wang et al., 1998, "Odorant receptors govern the formation of a precise topographic map", Cell, 93(1): 47-60.
Whissell-Buechy et al., 1973, "Odour-blindness to musk: simple recessive inheritance", Nature, 242(5395): 271-273.
Williams et al., 1991, "Introduction of foreign genes into tissues of living mice by DNA-coated microprojectiles", Proc Natl Acad Sci USA, 88:272.
Wilson et al., 1984, "The structure of an antigenic determinant in a protein", Cell, 37(3):767-778.
Wu and Wu, 1987, "Receptor-mediated in vitro gene transformation by a soluble DNA carrier system", J Biol Chem, 262(10): 4429-4432.
Wu and Wu, 1988, "Receptor-mediated gene delivery and expression in vivo", J Biol Chem, 263(29): 14621-14624.
Wu et al., 1992, "Hepatocyte-directed gene transfer in vivo leads to transient improvement of hypercholesterolemia in low density lipoprotein receptor-deficient rabbits", J Biol Chem, 267(2): 963-967.
Wyart et al., 2007, "Smelling a single component of male sweat alters levels of cortisol in women", J. Neurosci, 27 (6): 1261-1265.
Wysocki, C,J., et al., 1984, "Ability to smell androstenone is genetically determined", Proc Natl Acad Sci USA, 81 (15):4899-4902.
Young et al., 2002, "Different evolutionary processes shaped the mouse and human olfactory receptor gene families", Hum Mol Genet, 11(5): 535-546.
Zhang and Firestein, 2002, "The olfactory receptor gene superfamily of the mouse", Nat Neurosci, 5(2): 124-133.
Zhang et al., 1997, "Directed evolution of a fucosidase from a galactosidase by DNA shuffling and screening", Proc Natl Acad Sci USA, 94(9):4504-4509.
Zhao and Arnold, 1997, "Optimization of DNA shuffling for high fidelity recombination", Nuc Acids Res, 25 (6):1307-1308.
Zhao et al., 1998, "Functional expression of a mammalian odorant receptor", Science, 279(5348): 237-242.
Zuckennann et al., 1994, "Discovery of nanomolar ligands for 7-transmembrane G-protein-coupled receptors from a diverse N-(substituted)glycine peptoid library", J Med Chem, 37(17): 2678-2685.
Axel, 1995, "The molecular logic of smell", Sci Am 273(4): 154-159, Review.
Baker et al., 1994, "The cyclophilin homolog NinaA functions as a chaperone, forming a stable complex in vivo with its protein target rhodopsin", Embo J. 13(20): 4886-4895.
Ben-Bassat et al., 1987, "Processing of the initiation methionine from proteins: properties of the *Escherichia coli* methionine aminopeptidase and its gene structure", J. Bacteriol, 169(2):751-757.
Bozza et al., 2002, "Odorant receptor expression defines functional units in the mouse olfactory system", J. Neurosci 22(8): 3033-3043.
Brady and Limbird, 2002, "G protein-coupled receptor interacting proteins: roles in localization and signal transduction", Cell Signal, 14(4): 297-309.
Bremner et al., 2003, "The prevalence of androstenone anosmia", Chem Senses, 28(5): 423-432.
Buck and Axel, 1991, "A novel multigene family may encode odorant receptors: a molecular basis for odor recognition", Cell, 65(1): 175-187.
Cadwell and Joyce, 1992, "Randomization of genes by PCR mutagenesis", PCR Methods Appl, 2:28.
Caplen et al., 2001, "Specific inhibition of gene expression by small double-stranded RNAs in invertebrate and vertebrate systems", Proc Natl Acad Sci USA, 98(17): 9742-9247.
Caruthers et al., 1980, "New chemical methods for synthesizing polynucleotides", Nucl Acids Res Symp Ser, 7: 215-223.
Chow and Kempe, 1981, "Synthesis of oligodeoxyribonucleotides on silica gel support", Nucl Acids Res, 9 (12):2807-2817.
Crameri et al., 1996, "Improved green fluorescent protein by molecular evolution using DNA shuffling", Nat Biotechnol, 14(3): 315.
Crameri et al., 1997, "Molecular evolution of an arsenate detoxification pathway by DNA shuffling", Nat Biotechnol, 15(5): 436-438.
Crea and Horn, 1980, "Synthesis of oligonucleotides on cellulose by a phosphotriester method", Nucl Acids Res, 8 (10):2331-2348.
Curiel et al., 1992, "High-efficiency gene transfer mediated by adenovirus coupled to DNA-polylysine complexes", Hum Gene Ther, 3(2): 147-154.
Cwirla et al., 1990, "Peptides on phage: a vast library of peptides for identifying ligands", Proc Natl Acad Sci USA, 87(16):6378-6382.
Denyer et al., 1998, "HTS approaches to voltage-gated ion channel drug discovery", Drug Discov Today, 3: 323.
Devlin et al, 1990, "Random peptide libraries: a source of specific protein binding molecules", Science, 249(4967): 404-406.
Doty et al., 1995, "A study of the test-retest reliability of ten olfactory tests", Chem Senses, 20(6): 645-656.
Dravnieks et al., 1982, "Odor quality: semantically generated multi-dimensional profiles are stable", Science, 218 (4574): 799-801.
Eckert and Kunkel, 1991, "DNA polymerase fidelity and the polymerase chain reaction", PCR Methods Appl, 1(1): 17-24.
Elbashir et al., 2001, "RNA interference is mediated by 21- and 22-nucleotide RNAs", Genes Dev, 15(2): 188-200.
Elbashir et al., 2001, "Duplexes of 21-nucleotide RNAs mediate RNA interference in cultured mammalian cells", Nature, 411(6836): 494-498.
Elbashir et al., 2001, "Functional anatomy of siRNAs for mediating efficient RNAi in *Drosophila melanogaster* embryo lysate", Embo J. 20(23): 6877-6788.
Elbashir et al., 2002, "Analysis of gene function in somatic mammalian cells using small interfering RNAs", Methods, 26(2): 199-213.
Evans et al., 1989, "An engineered poliovirus chimaera elicits broadly reactive HIV-1 neutralizing antibodies", Nature, 339(6223): 385-388, 340.
Ferreira et al., 1996, "Cyclophilin-related protein RanBP2 acts as chaperone for red/green opsin", Nature, 383 (6601): 637-640.
Firestein, 2001, "How the olfactory system makes sense of scents", Nature, 413(6852):211-218.
Gaillard et al., 2002, "A single olfactory receptor specifically binds a set of odorant molecules", Eur J. Neurosci 15 (3), 409-418.
Gilbert et al., 1996, "Odor perception phenotypes: multiple, specific hyperosmias to musks", Chem Senses, 21(4): 411-416.
Gimelbrant et al., 2001, "Olfactory receptor trafficking involves conserved regulatory steps", J Biol Chem, 276(10): 7285-7290.
Gonzalez et al., 1999, "Cell-based assays and instrumentation for screening ion-channel targets", Drug Discov Today, 4(9):431-39.
Gower et al., 1998, in Perfumery (eds, Van Toiler, S, & Dodd, G,H,) 47-75 (Chapman & Hall, London, 1998).
Hatt et al., 1999, "Cloning, functional expression and characterization of a human olfactory receptor", Cell Mol Biol, 45(3): 285-291.
Huang et al., 1988, "Vaccinia virus recombinants expressing an 11-kilodalton beta-galactosidase fusion protein incorporate active beta-galactosidase in virus particles", J. Virol 62(10): 3855-3861.

Ike et al., 1983, "Solid phase synthesis of polynucleotides, VIII, Synthesis of mixed oligodeoxyribonucleotides by the phosphotriester solid phase method", Nucl Acid Res, 11(2):477-488.

Itakura et al., 1984, "Expression in *Escherichia coli* of a Chemically Synthesized Gene for the Hormone Somatostatin", Science, 198: 1056.

Itakura et al., 1984, "Synthesis and use of synthetic oligonucleotides", Annu Rev Biochem, 53: 323-356.

Kajiya et al., 2001, "Molecular bases of odor discrimination: Reconstitution of olfactory receptors that recognize overlapping sets of odorants", J Neurosci, 21(16): 6018-6025.

Keller et al., 2004, "A psychophysical test of the vibration theory of olfaction", Nat Neurosci, 7(4): 337-338.

Keller et al., 2004, "Human olfactory psychophysics", Curr Biol, 14(20): R875-878.

Keller et al., 2007, "Genetic variation in a human odorant receptor alters odour perception", Nature, 449(7161): 468-472.

Krautwurst et al., 1998, "Identification of ligands for olfactory receptors by functional expression of a receptor library", Cell, 95(7), 917-926.

Laird et al., 1988, "Evidence against the role of rhodopsin in rod outer segment binding to RPE cells", Invest Ophthalmol Vis Sci, 29(3): 419-428.

Lam, 1997, "Application of combinatorial library methods in cancer research and drug discovery", Anticancer Drug Des, 12(3): 145-167.

Leung et al., 1989, "A method for random mutagenesis of a defined DNA segment using a modified polymerase chain reaction", Technique, 1:11.

Loconto et al., 2003, "Functional expression of murine V2R pheromone receptors involves selective association with the M10 and M1 families of MHC class Ib molecules", Cell, 112(5): 607-618.

Lu et al., 2003, "Endoplasmic reticulum retention, degradation, and aggregation of olfactory G-protein coupled receptors", Traffic, 4(6): 416-433.

Malnic et al., 1999, "Combinatorial receptor codes for odors", Cell, 96(5): 713-723.

Matteucci and Caruthers, 1980, "The synthesis of oligodeoxyprimidines on a polymer support", Tetrahedron Lett, 21:719.

COMPOSITIONS AND METHODS FOR CHARACTERIZING AND REGULATING OLFACTORY SENSATION

CROSS-REFERENCE TO RELATED APPLICATION

This application is 371 U.S. national stage entry of pending International Patent Application No. PCT/US2008/063073, international filing date May 8, 2008, which claims priority to expired U.S. Provisional Application No. 60/928,249, filed May 8, 2007, all of which are herein incorporated by reference in their entireties.

STATEMENT REGARDING FEDERALLY SPONSORED RESEARCH OR DEVELOPMENT

This invention was made with government support under Grant Nos.: DC05782, and DC008480 awarded by the National Institutes of Health. The government has certain rights in the invention.

FIELD OF THE INVENTION

The present invention relates to the characterization of odorant receptors. In particular, the present invention relates to the OR7D4 proteins and nucleic acids encoding OR7D4 proteins and cell systems for screening for modulators of OR7D4 receptors. The present invention further provides assays for the detection of OR7D4 polymorphisms and mutations associated with altered olfactory sensation states, as well as methods of screening for therapeutic agents, ligands, and modulators of OR7D4 receptors.

BACKGROUND OF THE INVENTION

Olfactory sensation profoundly influences a person's quality of life. In addition to the aesthetic aspects of life associated with olfactory sensation, approximately 2 million Americans experience some type of olfactory dysfunction. Studies show that olfactory dysfunction affects at least 1% of the population under the age of 65 years, and well over 50% of the population older than 65 years. The sense of smell determines the flavor of foods and beverages and serves as an early warning system for the detection of environmental hazards, such as spoiled food, leaking natural gas, smoke, or airborne pollutants. The losses or distortions of smell sensation can adversely influence food preference, food intake and appetite.

Olfactory disorders are classified as follows: 1) anosmia: inability to detect qualitative olfactory sensations (e.g., absence of smell function), 2) partial anosmia: ability to perceive some, but not all, odorants, 3) hyposmia or microsmia: decreased sensitivity to odorants, 4) hyperosmia: abnormally acute smell function, 5) dysosmia (cacosmia or parosmia): distorted or perverted smell perception or odorant stimulation, 6) phantosmia: dysosmic sensation perceived in the absence of an odor stimulus (a.k.a. olfactory hallucination), and 7) olfactory agnosia: inability to recognize an odor sensation.

Olfactory dysfunction is further classified as 1) conductive or transport impairments from obstruction of nasal passages (e.g., chronic nasal inflammation, polyposis, etc.), 2) sensorineural impairments from damage to neuroepithelium (e.g., viral infection, airborne toxins, etc.), 3) central olfactory neural impairment from central nervous system damage (e.g., tumors, masses impacting on olfactory tract, neurodegenerative disorders, etc.). These categories are not mutually exclusive. For example, viruses can cause damage to the olfactory neuroepithelium and they may also be transported into the central nervous system via the olfactory nerve causing damage to the central elements of the olfactory system.

Smelling abilities are initially determined by neurons in the olfactory epithelium, the olfactory sensory neurons (hereinafter "olfactory neurons). In olfactory neurons, odorant receptor (hereinafter "OR") proteins, members of the G-protein coupled receptor (hereinafter "GPCR") superfamily, are synthesized in the endoplasmic reticulum, transported, and eventually concentrated at the cell surface membrane of the cilia at the tip of the dendrite. Considering that ORs have roles in target recognition of developing olfactory axons, OR proteins are also present at axon terminals (see, e.g., Mombaerts, P., (1996) Cell 87, 675-686; Wang, F., et al. (1998) Cell 93, 47-60; each herein incorporated by reference in their entireties). In rodents, odorants are transduced by as many as 1000 different ORs encoded by a multigene family (see, e.g., Axel, R. (1995) Sci Am 1273, 154-159; Buck, L., and Axel, R. (1991) Cell 65, 175-187; Firestein, S. (2001) Nature 413, 211-218; Mombaerts, P. (1999) Annu Rev Neurosci 22, 487-509; Young, J. M., et al., (2002) Hum Mol Genet. 11, 535-546; Zhang, X., and Firestein, S. (2002) Nat Neurosci 5, 124-133; each herein incorporated by reference in their entirety). Each olfactory neuron expresses only one type of the OR, forming the cellular basis of odorant discrimination by olfactory neurons (see, e.g., Lewcock, J. W., and Reed, R. R. (2004) Proc Natl Acad Sci USA; Malnic, B., et al., (1999) Cell 96, 713-723; Serizawa, S., et al., (2003) Science 302, 2088-2094; each herein incorporated by reference in their entirety).

What is needed is a better understanding of olfactory sensation. What is further needed is a better understanding of odorant receptor function.

SUMMARY OF THE INVENTION

Human olfactory perception differs enormously between individuals, with large reported perceptual variations in the intensity and pleasantness of a given odor. Androstenone (5α-androst-16-en-3-one), an odorous steroid derived from testosterone, is variously perceived by different individuals as offensive ("sweaty, urinous"), pleasant ("sweet, floral"), or odorless (e.g., Wysocki, C. J., et al., Proc Natl Acad Sci USA 81, 4899-4902 (1984); Gower, D. B., Nixon, A. & Mallet, A. I. in Perfumery (eds. Van Toller, S. & Dodd, G. H.) 47-75 (Chapman & Hall, London, 1998); Bremner, E. A., et al., Chem Senses 28, 423-432 (2003); each of which are herein incorporated by reference in their entireties). Up to 30% of humans have reduced sensitivity to androstenone, with 6% fitting the criteria of specific anosmia or "odor blindness" to androstenone, which may be a genetically determined trait (see, e.g., Wysocki, C. J., et al., Proc Natl Acad Sci USA 81, 4899-4902 (1984); Bremner, E. A., et al., Chem Senses 28, 423-432 (2003); Whissell-Buechy, D., et al., Nature 242, 271-273 (1973); each of which are herein incorporated by reference in their entireties. In experiments conducted during the course of the development of embodiments of the present invention, the human odorant receptor, OR7D4, was found to be selectively activated in vitro by androstenone and the related odorous steroid androstadienone (androsta-4,16-dien-3-one) and was found not respond to a panel of 64 other odors and two solvents. In addition, a common variant of OR7D4 (OR7D4 WM), which contains two non-synonymous single nucleotide polymorphisms (SNPs) resulting in two amino acid substitutions (R8SW, T133M), was found to have severely impaired olfactory function in vitro in the presence of androstenone and androstadienone. In addition, human subjects with RT/WM or WM/WM genotypes were found to be less sensitive to androstenone and androstadienone and found both odors less unpleasant than subjects with a functional RT/RT genotype. A second OR7D4 variant with reduced function in vitro (OR7D4 P79L), was found to have reduced sensitivity to androstenone in human subjects. An additional OR7D4 variant (OR7D4 S84N), a variant with increased function in vitro, was found to demonstrate increased sensitivity to androstenone and androstadienone. The present invention is not limited to a particular mechanism. Indeed, an understanding of the mechanism is not necessary to practice the present invention. Nonetheless, based upon experiments conducted during the course of the development of embodiments of the present invention, it was determined that polymorphisms in OR7D4 contribute to the variability in perception of steroidal odors (e.g., androstenone and androstadienone).

Accordingly, the present invention relates to the characterization of odorant receptors. In particular, the present invention relates to the OR7D4 proteins and nucleic acids encoding OR7D4 proteins and cell systems for screening for modulators of OR7D4 receptors. The present invention further provides assays for the detection of OR7D4 polymorphisms and mutations associated with altered olfactory sensation states, as well as methods of screening for therapeutic agents, ligands, and modulators of OR7D4 receptors.

In certain embodiments, the present invention provides a composition comprising an isolated and purified nucleic acid sequence encoding a protein comprising any one or more of OR7D4 wild type, OR7D4 WM (R188W/T133M), OR7D4 P79L, and OR7D4 S84N. In some embodiments, the sequence is operably linked to a heterologous promoter. In other embodiments, the sequence is contained within a vector. In further embodiments, the vector is within a host cell. In some embodiments, a functional receptor is expressed in the host cell.

In other embodiments, the nucleic acid comprises any one or more of OR7D4 wild type, OR7D4 WM (R188W/T133M), OR7D4 P79L, and OR7D4 S84N and variants thereof that are at least 80% identical to OR7D4 wild type, OR7D4 WM (R188W/T133M), OR7D4 P79L, and OR7D4 S84N. In some embodiments, the nucleic acid sequence is selected from the group consisting of OR7D4 wild type, OR7D4 WM (R188W/T133M), OR7D4 P79L, and OR7D4 S84N. In some embodiments, the nucleic acid sequence encodes a wild type OR7D4 polypeptide. In some embodiments, the nucleic acid sequence encodes an OR7D4 polypeptide having R88W and T133M amino acid substitutions. In some embodiments, the nucleic acid sequence encodes an OR7D4 polypeptide having a P79L amino acid substitution. In some embodiments, the nucleic acid sequence encodes an OR7D4 polypeptide having a D52G amino acid substitution. In some embodiments, the nucleic acid sequence encodes an OR7D4 polypeptide having a S75C amino acid substitution. In some embodiments, the nucleic acid sequence encodes an OR7D4 polypeptide having a M136I amino acid substitution. In some embodiments, the nucleic acid sequence encodes an OR7D4 polypeptide having a L162P amino acid substitution. In some embodiments, the nucleic acid sequence encodes an OR7D4 polypeptide having a A279D amino acid substitution. In some embodiments, the nucleic acid sequence encodes an OR7D4 polypeptide having a L292M amino acid substitution. In some embodiments, the nucleic acid sequence encodes an OR7D4 polypeptide having a H131Q amino acid substitution. In some embodiments, the nucleic acid sequence encodes an OR7D4 polypeptide having a C139Y amino acid substitution. In some embodiments, the nucleic acid sequence encodes an OR7D4 polypeptide having enhanced olfactory sensation. In some embodiments, the nucleic acid sequence encodes an OR7D4 polypeptide having diminished olfactory sensation.

The present invention also provides a composition comprising a polypeptide having an amino acid sequence comprising any one or more of OR7D4 wild type, OR7D4 WM (R188W/T133M), OR7D4 P79L, and OR7D4 S84N and variants thereof that are at least 80% identical to OR7D4 wild type, OR7D4 WM (R188W/T133M), OR7D4 P79L, and OR7D4 S84N. In some embodiments, the polypeptide is at least 90% identical to OR7D4 wild type, OR7D4 WM (R188W/T133M), OR7D4 P79L, and OR7D4 S84N. In other embodiments, the polypeptide is at least 95% identical OR7D4 wild type, OR7D4 WM (R188W/T133M), OR7D4 P79L, and OR7D4 S84N. In still other embodiments, the polypeptide is selected from the group consisting of OR7D4 wild type, OR7D4 WM (R188W/T133M), OR7D4 P79L, and OR7D4 S84N. In some embodiments, the polypeptide has one or more changes (e.g., 1, 2, 3, 4, 5, 6, etc.) or truncations or chimeras that retain one or more desired bioactivities (e.g., enhanced olfactory sensation, diminished olfactory sensation, expected olfactory sensation).

The present invention also provides a method of reducing OR7D4 activity comprising providing a target cell expressing OR7D4 protein (e.g., OR7D4, OR7D4 WM, OR7D4 P79L, OR7D4 D52G, OR7D4 S75C, OR7D4 M136I, OR7D4 L162P, OR7D4 A279D, and OR7D4 L292M, OR7D4H131Q, OR7D4 C139Y) and an agent that inhibits OR7D4 (e.g., by blocking ligand binding), and contacting the target cell with the composition thereby reducing OR7D4 activity. In some embodiments, the contacting is conducted in vitro (e.g., in culture) or in vivo. In some embodiments, the agent comprises a composition comprising a small interfering RNA duplex (siRNA), or a vector encoding said siRNA, that targets the OR7D4 mRNA. In further embodiments, the contacting is conducted under conditions such that the vector expresses the siRNA in the target cell. In still other embodiments, the composition further comprises a nucleic acid transfecting agent. In some embodiments, the agent is an antibody that inhibits OR7D4 (e.g., by blocking ligand binding). In some embodiments, the agent is a synthetic ligand that inhibits OR7D4 (e.g., by blocking ligand binding). In some embodiments, the agent is a peptide that inhibits OR7D4 (e.g., by blocking ligand binding). In some embodiments, the agent is competitive or non-competitive small molecule inhibitor of OR7D4.

The present invention also provides a method of increasing OR7D4 activity comprising providing a target cell expressing OR7D4 protein (e.g., OR7D4, OR7D4 WM, OR7D4 P79L, OR7D4 D52G, OR7D4 S75C, OR7D4 M136I, OR7D4 L162P, OR7D4 A279D, and OR7D4 L292M, OR7D4H131Q, OR7D4 C139Y) and an OR7D4 receptor ligand, and contacting the target cell with the OR7D4 receptor ligand thereby increasing OR7D4 activity. In some embodiments, the contacting is conducted in vitro (e.g., in culture) or in vivo. In some embodiments, the OR7D4 receptor ligand is a steroid (e.g., androstenone or androstadienone).

The present invention also provides a method comprising providing a subject with symptoms of altered olfactory sensation (e.g., altered ability to smell steroid odors), and an agent that modulates (e.g., enhances or diminishes) the effect of a OR7D4 protein (e.g., OR7D4 WM, OR7D4 P79L, OR7D4 D52G, OR7D4 S75C, OR7D4 M136I, OR7D4 L162P, OR7D4 A279D, and OR7D4 L292M, OR7D4H131Q, OR7D4 C139Y), and administering the agent to the subject under conditions such that the subject's olfactory sensation is modulated. In some embodiments, the agent comprises a composition comprising small interfering RNA duplexes (siRNAs), or vectors encoding said siRNAs, configured to inhibit expression of a OR7D4 protein (e.g., OR7D4, OR7D4 WM, OR7D4 P79L, OR7D4 D52G, OR7D4 S75C, OR7D4 M136I, OR7D4 L162P, OR7D4 A279D, and OR7D4 L292M, OR7D4H131Q, OR7D4 C139Y). In some embodiments, the agent is an antibody that modulates (e.g., enhances or diminishes) the effect of a OR7D4 protein. In some embodiments, the agent is a synthetic ligand that modulates (e.g., enhances or diminishes) the effect of a OR7D4 protein. In some embodiments, the agent is a peptide that modulates (e.g., enhances or diminishes) the effect of a OR7D4 protein. In some embodiments, the agent is competitive or non-competitive small molecule modulator of a OR7D4 protein. In other embodiments, the agent is administered intravenous, topically, and orally. In still further embodiments, the composition further comprises a nucleic acid transfecting agent. In still further embodiments, the composition further comprises reagents suitable for topcial administration (e.g., cream, aerosol, spray, etc.).

In some embodiments, the present invention provides transgenic animals (e.g., humans, cats, dogs, cows, primates, etc.) expressing one or more transgenes (e.g., olfactory sensation modulating transgenes) (e.g., OR7D4, OR7D4 WM, OR7D4 P79L, OR7D4 D52G, OR7D4 S75C, OR7D4 M136I, OR7D4 L162P, OR7D4 A279D, and OR7D4 L292M, OR7D4H131Q, OR7D4 C139Y). In some embodiments, the transgenes cause enhanced OR7D4 activity in the animal. In some embodiments, the transgenes cause diminished OR7D4 activity in the animal. In some embodiments, the transgene is provided to an animal that otherwise does not have OR7D4 activity.

The present invention also provides a method comprising providing a subject at risk for developing altered olfactory sensation (e.g., altered ability to smell steroid odors), and an agent that modulates (e.g., enhances or diminishes) the effect of a OR7D4 proteins (e.g., OR7D4, OR7D4 WM, OR7D4 P79L, OR7D4 D52G, OR7D4 S75C, OR7D4 M136I, OR7D4 L162P, OR7D4 A279D, and OR7D4 L292M, OR7D4H131Q, OR7D4 C139Y), and administering the agent to the subject under conditions such that the subject is prevented from developing altered olfactory sensation. In some embodiments, the agent comprises a composition comprising small interfering RNA duplexes (siRNAs), or a vector encoding said siRNA, configured to inhibit expression of OR7D4 protein. In some embodiments, the agent is an antibody that modulates (e.g., enhances or diminishes) the effect of a OR7D4 protein. In some embodiments, the agent is a synthetic ligand that modulates (e.g., enhances or diminishes) the effect of a OR7D4 protein. In some embodiments, the agent is a peptide that modulates (e.g., enhances or diminishes) the effect of a OR7D4 protein. In some embodiments, the agent is competitive or non-competitive small molecule modulator of a OR7D4 protein. In other embodiments, the agent is administered intravenous, topically, and orally. In still further embodiments, the composition further comprises a nucleic acid transfecting agent. In still further embodiments, the composition further comprises reagents suitable for topcial administration (e.g., cream, aerosol, spray, etc.).

The present invention further provides a composition comprising small interfering RNA duplexes (siRNAs), or vectors encoding said siRNA, configured to inhibit expression, transport or function of OR7D4 protein (e.g., OR7D4, OR7D4 WM, OR7D4 P79L, OR7D4 D52G, OR7D4 S75C, OR7D4 M136I, OR7D4 L162P, OR7D4 A279D, and OR7D4 L292M, OR7D4H131Q, OR7D4 C139Y). In some embodiments, the compositions comprise a nucleic acid transfecting agent.

The present invention also provides a kit comprising a composition, wherein said composition modulates (e.g., enhances or diminishes) expression of OR7D4 protein (e.g., OR7D4, OR7D4 WM, OR7D4 P79L, OR7D4 D52G, OR7D4 S75C, OR7D4 M136I, OR7D4 L162P, OR7D4 A279D, and OR7D4 L292M, OR7D4H131Q, OR7D4 C139Y). In some embodiments, the kit comprises printed material with instructions for employing said composition. In some embodiments, the composition comprises an agent that modulates (e.g., enhances or diminishes) the effect of a OR7D4 protein. In some embodiments, the agent is an antibody that modulates (e.g., enhances or diminishes) the effect of a OR7D4 protein. In some embodiments, the agent is a synthetic ligand that modulates (e.g., enhances or diminishes) the effect of a OR7D4 protein. In some embodiments, the agent is a peptide that modulates (e.g., enhances or diminishes) the effect of a OR7D4 protein. In some embodiments, the agent is competitive or non-competitive small molecule modulator of a OR7D4 protein. In other embodiments, the agent is administered intravenous, topically, and orally. In still further embodiments, the composition further comprises a nucleic acid transfecting agent. In still further embodiments, the composition further comprises reagents suitable for topcial administration (e.g., cream, aerosol, spray, etc.). In some embodiments, the composition comprises small interfering RNA duplexes (siRNAs), or vector encoding said siRNAs, configured to modulate (e.g., enhance or diminish) expression of OR7D4 protein.

The present invention also provides a method for producing variants of OR7D4 comprising providing a nucleic acid sequence comprising one or more of OR7D4 wild type, OR7D4 WM (R188W/T133M), OR7D4 P79L, and OR7D4 S84N, mutagenizing the nucleic acid sequence, and screening the variant for OR7D4 activity.

The present invention further provides a method for screening compounds for the ability to alter OR7D4 activity comprising providing a polypeptide sequence comprising at least a portion of OR7D4, one or more test compounds, and combining in any order, the polypeptide sequence comprising at least a portion of OR7D4, and the one or more test compounds under conditions such that the polypeptide sequence, and the test compound interact, and measuring OR7D4 activity.

The present invention further provides a method for identifying pharmaceutical agents useful for modulating olfactory sensation, comprising providing target cells, wherein the target cells comprise a OR7D4 polypeptide (e.g., OR7D4, OR7D4 WM, OR7D4 P79L, OR7D4 D52G, OR7D4 S75C, OR7D4 M136I, OR7D4 L162P, OR7D4 A279D, and OR7D4 L292M, OR7D4H131Q, OR7D4 C139Y), and a candidate pharmaceutical agent, and exposing the target cells to the candidate pharmaceutical agents, measuring the activity of said OR7D4 polypeptide of said target cells, and selecting candidate pharmaceutical agents that inhibit, stimulate or enhance the activity of the OR7D4 polypeptide. In other embodiments, the method is used for identifying olfactory sensation disorders.

The present invention also provides a method for diagnosing altered olfactory sensation, comprising detecting the presence or absence of a polymorphism associated with OR7D4 gene in a sample. In some embodiments, the polymorphism is in the coding region of said OR7D4 gene. In further embodiments, the polymorphism is selected from the group consisting of OR7D4, OR7D4 WM, OR7D4 P79L, OR7D4 D52G, OR7D4 S75C, OR7D4 M136I, OR7D4 L162P, OR7D4 A279D, and OR7D4 L292M, OR7D4H131Q, OR7D4 C139Y.

In other embodiments, the polymorphism disturbs OR7D4 mRNA composition or stability. In some embodiments, the polymorphism alters OR7D4 protein sequence including amino acid substitutions, premature protein termination, and aberrant OR7D4 mRNA splicing leading to altered OR7D4 protein sequence.

In other embodiments, the detecting comprises detecting the polymorphism in a nucleic acid from said sample. In further embodiments, the sample is DNA. In other embodiments, the sample is RNA.

In further embodiments, the detecting comprises detecting a polymorphic protein. In still further embodiments, the detecting a polymorphic protein occurs with an antibody.

Androstadienone is present in the sweat of men and has been suggested to be a chemosignal in humans. Indeed, cortisol levels in women smelling androstadienone are maintained at higher levels than in women not smelling androstadienone (see, e.g., Wyart, C., et al., J. Neuroscience 2007 27(6):1261-1265; herein incorporated by reference in its entirety). As such, it is contemplated that individuals having altered OR7D4 activity (e.g., individuals having the OR7D4 S84N variant) have reduced or enhanced ability to smell androstadienone and have different responses to stimulation by OR7D4 ligands. Likewise, natural or synthetic ligands to the receptor may be used to stimulate desired biological response. As such, in some embodiments, the present invention provides methods for increasing cortisol expression in subjects through administering agents that activate or enhance OR7D4 activity. In some embodiments, the present invention provides methods for treating cortisol related disorders (e.g., Addisons disease, Cushing's Syndrome, inflammatory disorders) through administration of agents that modulate (e.g., diminish or enhance) OR7D4 activity. Moreover, as cortisol expression is related to hormonal sex drive, methods for modulating sex drive (e.g., increasing or decreasing) are provided through administration of agents that modulate (e.g., enhance or diminish) OR7D4 activity.

In certain embodiments, the present invention provides personal application agents (e.g., perfumes, colognes, deodorants, soaps, lotions, personal lubricants, shampoos, hair gels, inhalants, topical medications, aerosol sprays, pot pouri, room deoderizers, scented candles, etc.) configured to modulate OR7D4 activity. For example, in some embodiments, the personal application agents comprise steroid agents or other OR7D4 ligands such as androstenone and androstadienone and analogues thereof. The present invention is not limited to particular types or kinds of steroid agents (e.g., naturally occurring steroids, synthetic steroids). In some embodiments the steroid agents include naturally occurring and/or synthetic androstenone and androstadienone. In some embdodiments, the personal application agents of the present invention may be used to increase female sex drive through enhancing of cortisol expression and OR7D4 activity. In some embodiments, the personal application agents can be used to increase a subject's desire to mate through modulation of the subject's OR7D4 activity. OR7D4 ligand may be optimized or used in combination to have maximum desired impact on subject with a particular type of OR7D4 receptor.

In certain embodiments, the present invention provides methods for developing personalized personal application agents (e.g., perfumes, colognes, deodorants, soaps, lotions, personal lubricants, shampoos, hair gels, inhalants, topical medications, aerosol sprays, pot pouri, room deoderizers, scented candles, etc.) specific for a particular OR7D4 genotype. In some embodiments, a subject may develop a personal application agent that is specific for a different subject's OR7D4 genotype. In some embodiments, a subject may develop a personal application agent that is specific to that subject's OR7D4 genotype. Such personal application agents and related methods find use in a wide variety of settings including cosmetic research settings, medical research settings, and domestic research settings. In some embodiments, the methods are used to identify new polymorphisms of OR7D4.

BRIEF DESCRIPTION OF THE DRAWINGS

FIG. 1 shows that OR7D4 is a human odorant receptor selectively activated by androstenone and androstadienone.

FIG. 2 shows functional characterization of polymorphisms in OR7D4.

FIG. 2B, Relative intensity ratings for five odors from a for OR7D4 RT/RT, RT/M, and WM/WM subjects, compared to solvent (propylene glycol). Mean±S.E.M.

FIG. 4 shows OR7D4 WM correlates with changes in quality perception of androstenone and androstadlenone.

FIG. 5 shows OR7D4 P79L and S84N polymorphisms affect androstenone and androstadienone activity in vitro and perception in vivo.

FIG. 6 shows RT/P79L and RT/S84N intensity and valence rating.

DEFINITIONS

Figure 1A:
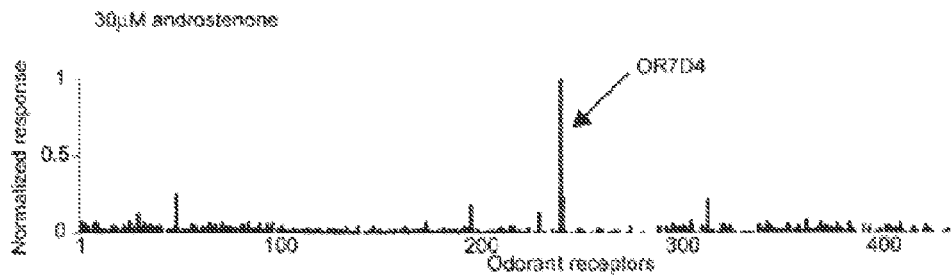
FIG. 1A, Luciferase assays of a panel of 432 samples including 337 unique human odorant receptors, 45 odorant receptor pseudogenes, 27 variant pairs of the same genes, 14 duplicates, and 9 negative controls, all expressed in Hana3A cells stimulated with 30 pM androstenone. OR7D4 produced the most robust response. Y-axis denotes normalized response.

To facilitate understanding of the invention, a number of terms are defined below.

As used herein, the term "odorant receptor" refers to odorant receptors generated from olfactory sensory neurons. Examples of odorant receptors include, but are not limited to, OR7D4, S6/79, S18, S46, S50, MOR23-1, MOR31-4, MOR31-6, MOR32-5 and MOR32-11.

As used herein, the term "odorant receptor cell surface localization" or equivalent terms refer to the molecular transport of an odorant receptor to a cell surface membrane. Examples of cell surface localization includes, but is not limited to, localization to cilia at the tip of a dendrite, and localization to an axon terminal.

As used herein, the term "olfactory disorder," "olfactory dysfunction," "olfactory disease" or similar term refers to a disorder, dysfunction or disease resulting in a diminished olfactory sensation (e.g., smell aberration). Examples of olfactory disorders, dysfunctions and/or diseases include, but are not limited to, head trauma, upper respiratory infections, tumors of the anterior cranial fossa, Kallmann syndrome, Foster Kennedy syndrome, Parkinson's disease, Alzheimer's disease, Huntington chorea, and exposure to toxic chemicals or infections. Diminished olfactory sensation is classified as anosmia—absence of smell sensation; hyposmia—decreased smell sensation; dysosmia—distortion of smell sensation; cacosmia—sensation of a bad or foul smell; and parosmia—sensation of smell in the absence of appropriate stimulus.

As used herein, the term "OR7D4" when used in reference to a protein or nucleic acid refers to a OR7D4 protein or nucleic acid encoding a OR7D4 protein of the present invention. The term OR7D4 encompasses both proteins that are identical to wild-type OR7D4 and variants of OR7D4 (e.g., OR7D4 WM, OR7D4 P79L, OR7D4 D52G, OR7D4 S75C, OR7D4 M136I, OR7D4 L162P, OR7D4 A279D, and OR7D4 L292M, OR7D4 H131Q, OR7D4 C139Y) or chimeric genes constructed with portions of OR7D4 coding regions). In some embodiments, the "OR7D4" is a wild type OR7D4 nucleic acid (mRNA) or polypeptide encoded by the wild type amino acid sequence. In other embodiments, the "OR7D4" is a variant or mutant nucleic acid or amino acid (e.g., OR7D4 WM, OR7D4 P79L, OR7D4 D52G, OR7D4 S75C, OR7D4

M136I, OR7D4 L162P, OR7D4 A279D, and OR7D4 L292M, OR7D4 H131Q, OR7D4 C139Y, OR7D4 S84N).

As used herein, the terms "subject" and "patient" refer to any animal, such as a mammal like a dog, cat, bird, livestock, and preferably a human. Specific examples of "subjects" and "patients" include, but are not limited to, individuals with an olfactory disorder, and individuals with olfactory disorder-related characteristics or symptoms.

As used herein, the phrase "symptoms of an olfactory disorder" and "characteristics of an olfactory disorder" include, but are not limited to, a diminished olfactory sensation (e.g., smell aberration).

The phrase "under conditions such that the symptoms are reduced" refers to any degree of qualitative or quantitative reduction in detectable symptoms of olfactory disorders, including but not limited to, a detectable impact on the rate of recovery from disease, or the reduction of at least one symptom of an olfactory disorder.

The term "siRNAs" refers to short interfering RNAs. Methods for the use of siRNAs are described in U.S. Patent App. No.: 20030148519/A1 (herein incorporated by reference). In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "gene" refers to a nucleic acid (e.g., DNA) sequence that comprises coding sequences necessary for the production of a polypeptide, RNA or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "complementary" or "complementarity" are used in reference to polynucleotides (i.e., a sequence of nucleotides) related by the base-pairing rules. For example, for the sequence 5'-"A-G-T-3'," is complementary to the sequence 3'-"T-C-A-S'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Complementarity can include the formation of base pairs between any type of nucleotides, including non-natural bases, modified bases, synthetic bases and the like.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The present invention is not limited to the hybridization of probes of about 500 nucleotides in length. The present invention contemplates the use of probes between approximately 10 nucleotides up to several thousand (e.g., at least 5000) nucleotides in length. One skilled in the relevant understands that stringency conditions may be altered for probes of other sizes (See e.g., Anderson and Young, Quantitative Filter Hybridization, in *Nucleic Acid Hybridization* [1985] and Sambrook et al., Molecular Cloning: A Laboratory Manual, Cold Spring Harbor Press, NY [1989]).

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "detection assay" refers to an assay for detecting the presence or absence of variant nucleic acid or amino acid sequences (e.g., polymorphisms or mutations) (e.g., an odorant receptor gene).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding odorant receptors includes, by way of example, such nucleic acid in cells ordinarily expressing odorant receptors where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, the term "purified" or "to purify" refers to the removal of contaminants from a sample. For example, odorant receptor antibodies are purified by removal of contaminating non-immunoglobulin proteins; they are also purified by the removal of immunoglobulin that does not bind a specific odorant receptor polypeptide. The removal of non-immunoglobulin proteins and/or the removal of immunoglobulins that do not bind a specific odorant receptor polypeptide results in an increase in the percent of specific odorant receptor-reactive immunoglobulins in the sample. In another example, recombinant odorant receptor polypeptides are expressed in bacterial host cells and the polypeptides are purified by the removal of host cell proteins; the percent of recombinant odorant receptor polypeptides is thereby increased in the sample.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 10, for a protocol for performing Northern blot analysis).

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

DETAILED DESCRIPTION OF THE INVENTION

The olfactory system represents one of the oldest sensory modalities in the phylogenetic history of mammals. Olfaction is less developed in humans than in other mammals such as rodents. As a chemical sensor, the olfactory system detects food and influences social and sexual behavior. The specialized olfactory epithelial cells characterize the only group of neurons capable of regeneration. Activation occurs when odiferous molecules come in contact with specialized processes known as the olfactory vesicles. Within the nasal cavity, the turbinates or nasal conchae serve to direct the inspired air toward the olfactory epithelium in the upper posterior region. This area (only a few centimeters wide) contains more than 100 million olfactory receptor cells. These specialized epithelial cells give rise to the olfactory vesicles containing kinocilia, which serve as sites of stimulus transduction.

There are three specialized neural systems are present within the nasal cavities in humans: 1) the main olfactory system (cranial nerve I), 2) trigeminal somatosensory system (cranial nerve V), 3) the nervus terminalis (cranial nerve 0). CN I mediates odor sensation. It is responsible for determining flavors. CN V mediates somatosensory sensations, including burning, cooling, irritation, and tickling. CN 0 is a ganglionated neural plexus. It spans much of the nasal mucosa before coursing through the cribriform plate to enter the forebrain medial to the olfactory tract. The exact function of the nervus terminalis is unknown in humans.

The olfactory neuroepithelium is a pseudostratified columnar epithelium. The specialized olfactory epithelial cells are the only group of neurons capable of regeneration. The olfactory epithelium is situated in the superior aspect of each nostril, including cribriform plate, superior turbinate, superior septum, and sections of the middle turbinate. It harbors sensory receptors of the main olfactory system and some CN V free nerve endings. The olfactory epithelium loses its general homogeneity postnatally, and as early as the first few weeks of life metaplastic islands of respiratory-like epithelium appear. The metaplasia increases in extent throughout life. It is presumed that this process is the result of insults from the environment, such as viruses, bacteria, and toxins.

There are 6 distinct cells types in the olfactory neuroepithelium: 1) bipolar sensory receptor neurons, 2) microvillar cells, 3) supporting cells, 4) globose basal cells, 5) horizontal basal cells, 6) cells lining the Bowman's glands. There are approximately 6,000,000 bipolar neurons in the adult olfactory neuroepithelium. They are thin dendritic cells with rods containing cilia at one end and long central processes at the other end forming olfactory fila. The olfactory receptors are located on the ciliated dendritic ends. The unmyelinated axons coalesce into 40 bundles, termed olfactory fila, which are ensheathed by Schwann-like cells. The fila transverses the cribriform plate to enter the anterior cranial fossa and constitute CN I. Microvillar cells are near the surface of the neuroepithelium, but the exact functions of these cells are unknown. Supporting cells are also at the surface of the epithelium. They join tightly with neurons and microvillar cells.

They also project microvilli into the mucus. Their functions include insulating receptor cells from one another, regulating the composition of the mucus, deactivating odorants, and protecting the epithelium from foreign agents. The basal cells are located near the basement membrane, and are the progenitor cells from which the other cell types arise. The Bowman's glands are a major source of mucus within the region of the olfactory epithelium.

The odorant receptors are located on the cilia of the receptor cells. Each receptor cell expresses a single odorant receptor gene. There are approximately 1,000 classes of receptors at present. The olfactory receptors are linked to the stimulatory guanine nucleotide binding protein Golf. When stimulated, it can activate adenylate cyclase to produce the second messenger cAMP, and subsequent events lead to depolarization of the cell membrane and signal propagation. Although each receptor cell only expresses one type of receptor, each cell is electrophysiologically responsive to a wide but circumscribed range of stimuli. This implies that a single receptor accepts a range of molecular entities.

The olfactory bulb is located on top of the cribriform plate at the base of the frontal lobe in the anterior cranial fossa. It receives thousands of primary axons from olfactory receptor neurons. Within the olfactory bulb, these axons synapse with a much smaller number of second order neurons which form the olfactory tract and project to olfactory cortex. The olfactory cortex includes the frontal and temporal lobes, thalamus, and hypothalamus.

Although mammalian ORs were identified over 10 years ago, little is known about the selectivity of the different ORs for chemical stimuli, mainly because it has been difficult to express ORs on the cell surface of heterologous cells and assay their ligand-binding specificity (see, e.g., Mombaerts, P. (2004) Nat Rev Neurosci 5, 263-278; herein incorporated by reference in its entirety). The reason is that OR proteins are retained in the ER and subsequently degraded in the proteosome (see, e.g., Lu, M., et al., (2003) Traffic 4, 416-433; McClintock, T. S., (1997) Brain Res Mol Brain Res 48, 270-278; each herein incorporated by reference in their entireties). Despite these difficulties, extensive efforts have matched about 20 ORs with cognate ligands with various degrees of certainty (see, e.g., Bozza, T., et al., (2002) J Neurosci 22, 3033-3043; Gaillard, I., et al., (2002) Eur J Neurosci 15, 409-418; Hatt, H., et al., (1999) Cell Mol Biol 45, 285-291; Kajiya, K., et al., (2001) J Neurosci 21, 6018-6025; Krautwurst, D., et al., (1998) Cell 95, 917-926; Malnic, B., et al., (1999) Cell 96, 713-723; Raming, K., et al., (1993) Nature 361, 353-356; Spehr, M., et al., (2003) Science 299, 2054-2058; Touhara, K., et al., (1999) Proc Natl Acad Sci USA 96, 4040-4045; Zhao, H., et al., (1998) Science 279, 237-242; each herein incorporated by reference in their entirety). Adding the 20 N-terminal amino acids of rhodopsin (e.g., Rho-tag) or a foreign signal peptide to the N-terminus facilitates surface expression of some ORs in heterologous cells (see, e.g., Hatt, H., et al., (1999) Cell Mol Biol 45, 285-291; Krautwurst, D., et al., (1998) Cell 95, 917-926; each herein incorporated in their entirety). However, for most ORs, modifications do not reliably promote cell-surface expression. For example, ODR-4, which is required for proper localization of chemosensory receptors in C. elegans, has a small effect on facilitating cell-surface expression of one rat OR, but not another OR (see, e.g., Gimelbrant, A. A., et al., (2001) J Biol Chem 276, 7285-7290; herein incorporated by reference). These findings indicate that olfactory neurons have a selective molecular machinery that promotes proper targeting of OR proteins to the cell surface, but no components of this machinery have been identified (see, e.g., Gimelbrant, A. A., et al., (2001) J Biol Chem 276, 7285-7290; McClintock, T. S., and Sammeta, N. (2003) Neuroreport 14, 1547-1552; each herein incorporated by reference in their entirety).

For some GPCRs, accessory proteins are required for correct targeting to the cell surface membrane (see, e.g., Brady, A. E., and Limbird, L. E. (2002) Cell Signal 14, 297-309; herein incorporated by reference in its entirety). These proteins include NinaA for Drosophila Rhodopsin (see, e.g., Baker, E. K., et al., (1994) Embo J 13, 4886-4895; Shieh, B. H., et al., (1989) Nature 338, 67-70; each herein incorporated by reference in their entirety), RanBP2 for mammalian cone opsin (see, e.g., Ferreira, P. A., et al., (1996) Nature 383, 637-640; herein incorporated by reference in its entirety), RAMPs for the mammalian calcitonin receptor-like receptor (CRLR) (see, e.g., McLatchie, L. M., et al., (1998) Nature 393, 333-339; herein incorporated by reference in its entirety) and finally the M10 family of MHC class I proteins and beta 2 microglobulin for V2R5, the putative mammalian pheromone receptors (see, e.g., Loconto, J., et al., (2003) Cell 112, 607-618; herein incorporated by reference in its entirety). With the exception of NinaA and RanBP2, none of these accessory proteins share any sequence homology to with each other; their only common feature is their association with the membrane.

Continued progress in understanding olfactory coding has been significantly hampered by the inability to functionally express ORs in heterologous cells in order to identify cognate ligands. To overcome this problem, three transmembrane proteins, REEP1, RTP1, and RTP2, as well as variants thereof, were identified that promote functional cell surface expression of ORs in 293T cells (see, e.g., U.S. Patent Application Publication No. 2006/0057640; herein incorporated by reference in its entirety). REEP and/or RTP are expressed specifically by olfactory neurons in the olfactory epithelium. REEP1 and RTP1 interacts with OR proteins. Using cells expressing REEP1 and RTP1 and RTP2, new ORs that respond to aliphatic odorants were identified (see, e.g., U.S. Patent Application Publication No. 2006/0057640; herein incorporated by reference in its entirety).

The characterization of ORs (e.g., the identification of odiferous agents for which an OR and/or a variant OR form is responsive) (e.g., the degree of which an OR and/or a variant OR form is responsive to a particular odiferous agent) provides numerous research, diagnostic, drug screening, and therapeutic applications. For example, the present invention permits the selective and controllable presentation of ORs and/or variant OR forms on test cells to, among other things, identify new odiferous agents for which the OR is responsive, to characterize ORs and variant OR forms, identify OR ligands, correlate olfactory responses to the molecular interactions underlying such response, identify and characterize groups of ORs and ligands responsible for olfactory responses and health conditions, and identify, select, and characterize regulators of OR response to study and control olfactory responses. The present invention, also, thus provides means for manipulating olfactory responses and the molecular basis for such response in vitro and in vivo. Numerous commercial applications are thus made possible, including the production, characterization, and use of in vitro or in vivo cell arrays expressing desired localized ORs for screening (e.g., high-throughput screening) compounds or use as synthetic olfactory systems. Any industry, including food industries, health industries, cosmetic industries, militaries, sanitary agencies, animal sniffers (e.g., for drugs, explosives, accident victims, etc.), among many others will find use of the compositions and methods of the present invention.

Inhibitors (e.g., antibodies, small molecules, aptamers, etc.) of OR/ligand interactions that are identified by the methods of the present invention find many uses. For example, the present invention provides a systematic way to identify which receptors and ligands are responsible for particular olfactory sensations (e.g., perceived scents). Thus, for example, by blocking particular interactions (e.g., via a nasal spray having the inhibitors) or enhancing particular interactions (e.g., via a nasal spray that provides certain ligands or a coating on the surface of an object that emits certain ligands) one can control perceived scents. Thus, undesired scents can be blocked, covered, or altered (e.g., a sniffer dog can be treated so as to only smell a target of interested and no other distracting smells, a sanitary worked can be made immune to the scent of waste, etc.) and desired scents can be enhanced.

In experiments conducted during the course of the development of embodiments of the present invention, the human odorant receptor, OR7D4, was found to be selectively activated in vitro by androstenone and the related odorous steroid androstadienone (androsta-4,16-dien-3-one) and was found not respond to a panel of 64 other odors and two solvents. In addition, a common variant of OR7D4 (OR7D4 WM), which contains two non-synonymous single nucleotide polymorphisms (SNPs) resulting in two amino acid substitutions (R8SW, T133M), was found to have severely impaired olfactory function in vitro in the presence of androstenone and androstadienone. In addition, human subjects with RT/WM or WM/WM genotypes were found to be less sensitive to androstenone and androstadienone and found both odors less unpleasant than subjects with a functional RT/RT genotype. A second OR7D4 variant with reduced function in vitro (OR7D4 P79L), was found to have reduced sensitivity to androstenone in human subjects. An additional OR7D4 variant (OR7D4 S84N), a variant with increased function in vitro, was found to demonstrate increased sensitivity to androstenone and androstadienone. The present invention is not limited to a particular mechanism. Indeed, an understanding of the mechanism is not necessary to practice the present invention. Nonetheless, based upon experiments conducted during the course of the development of embodiments of the present invention, it was determined that polymorphisms in OR7D4 contribute to the variability in perception of steroidal odors (e.g., androstenone and androstadienone).

Accordingly, embodiments of the present invention relate to the characterization of odorant receptors. In particular, embodiments of the present invention relate to the OR7D4 proteins and nucleic acids encoding OR7D4 proteins. The present invention further provides assays for the detection of OR7D4 polymorphisms and mutations associated with altered olfactory sensation states, as well as methods of screening for therapeutic agents, ligands, and modulators of OR7D4 proteins.

As cortisol levels in women smelling androstadienone are maintained at higher levels than in women not smelling androstadienone (see, e.g., Wyart, C., et al., J. Neuroscience 2007 27(6):1261-1265; herein incorporated by reference in its entirety), the present invention provides methods for increasing cortisol expression in subjects through administering agents that enhance or stimulate OR7D4 activity. In some embodiments, the present invention provides methods for treating cortisol related disorders (e.g., Addisons disease, Cushing's Syndrome, inflammatory disorders) through administration of agents that modulate (e.g., diminish or enhance) OR7D4 activity. In some embodiments, womens sex drives are increased by administering agents that enhance OR7D4 activity. In some embodiments, women's sex drives are diminished through administration of agents that reduce OR7D4 activity.

Exemplary compositions and methods of the present invention are described in more detail in the following sections: I. OR7D4 Polynucleotides; II. OR7D4 Polypeptides; IV. Detection of OR7D4 Alleles; V. Generation of OR7D4 Antibodies; VI. Gene Therapy Using OR7D4; VII. Transgenic Animals Expressing Exogenous OR7D4 Genes and Homologs, Mutants, and Variants Thereof; VIII. Drug Screening Using OR7D4; IX. Pharmaceutical Compositions Containing OR7D4 Nucleic Acid, Peptides, and Analogs; X. RNA Interference (RNAi); and XI. Consumer Applications.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. OR7D4 Polynucleotides

As described above, the present invention provides OR7D4 and variant OR7D4 proteins, and nucleic acid molecules encoding them. In particular, the present invention provides wild type OR7D4 genes and polypeptides and variant OR7D4 forms (see Table 1).

TABLE 1

Single Nucleotide Polymorphisms in OR7D4

| SNP | dbSNP ID | Allele | AA change | Codon | Protein region | Allele frequency** |
|---|---|---|---|---|---|---|
| refseq | | | | | | 0.788 |
| 1 | | T/C | D52G | 2 | IC1 | 0.002 |
| 2 | rs5020281 | G/C | S75C | 2 | TM2 | 0 |
| 3 | | G/A | P79L | 2 | TM2 | 0.042 |
| 4 | rs5020280 | C/T | S84N | 2 | EC1 | 0.012 |
| 5 | | G/A | R88W | 1 | EC1 | 0.154 |
| 6 | rs5020279 | G/C | H131Q | 3 | IC2 | 0 |
| 7 | rs5020278 | G/A | T133M | 2 | IC2 | 0.154 |
| 8 | rs5020277 | C/T | M136I | 3 | IC2 | 0 |
| 9 | rs5020276 | A/G | C139R | 1 | IC2 | 0 |
| 10 | rs5020275 | C/T | C139Y | 2 | IC2 | 0 |
| 11 | | A/G | L162P | 2 | TM4 | 0.001 |
| 12 | | G/T | A279D | 2 | TM7 | 0* |
| 13 | rs4564704 | G/T | L292M | 1 | TM7 | 0 |

Accordingly, the present invention provides nucleic acids encoding OR7D4 genes, homologs, variants (e.g., polymorphisms and mutants), including but not limited to, those described in OR7D4 wild type, OR7D4 WM (R188W/T133M), OR7D4 P79L, and OR7D4 S84N. In some embodiments, the present invention provides polynucleotide sequences that are capable of hybridizing to OR7D4 wild type, OR7D4 WM (R188W/T133M), OR7D4 P79L, and OR7D4 S84N under conditions of low to high stringency as long as the polynucleotide sequence capable of hybridizing encodes a protein that retains a biological activity of the naturally occurring OR7D4 protein. In some embodiments, the protein that retains a biological activity of a naturally occurring OR7D4 is 70% homologous to the wild-type OR7D4, preferably 80% homologous to the wild-type OR7D4, more preferably 90% homologous to the wild-type OR7D4, and most preferably 95% homologous to wild-type the OR7D4. In some embodiments, hybridization conditions are based on the melting temperature ($T_m$) of the nucleic acid binding complex and confer a defined "stringency" as explained above (see e.g., Wahl, et al., Meth. Enzymol., 152: 399-407 (1987), incorporated herein by reference).

In other embodiments of the present invention, additional alleles of OR7D4 genes are provided. In some embodiments, alleles result from a polymorphism or mutation (i.e., a change in the nucleic acid sequence) and generally produce altered mRNAs or polypeptides whose structure or function may or may not be altered (see, Table 1). Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence. Additional examples include truncation mutations (e.g., such that the encoded mRNA does not produce a complete protein).

In still other embodiments of the present invention, the nucleotide sequences of the present invention may be engineered in order to alter a OR7D4 coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

It is contemplated that it is possible to modify the structure of a peptide having a function (e.g., OR7D4 function) for such purposes as altering the biological activity (e.g., altering an olfactory response to androstenone and/or androstadienone). Such modified peptides are considered functional equivalents of peptides having an activity of a OR7D4 peptide as defined herein (e.g., wild type OR7D4 or a variant form of OR7D4). A modified peptide (e.g., wild type OR7D4 or a variant form of OR7D4) can be produced in which the nucleotide sequence encoding the polypeptide has been altered, such as by substitution, deletion, or addition. In some embodiments, these modifications do not significantly reduce the biological activity of the modified OR7D4 genes (e.g., wild type OR7D4 or a variant form of OR7D4). In other words, construct "X" can be evaluated in order to determine whether it is a member of the genus of modified or variant OR7D4 of the present invention as defined functionally, rather than structurally. In some embodiments, the activity of variant OR7D4 polypeptides is evaluated by methods described herein (e.g., the generation of transgenic animals or the use of signaling assays).

Moreover, as described above, variant forms of OR7D4 genes are also contemplated as being equivalent to those peptides and DNA molecules that are set forth in more detail herein (e.g., wild type OR7D4 or a variant form of OR7D4). For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of OR7D4 containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur -containing (cysteine and methionine) (e.g., Stryer ed., Biochemistry, pg. 17-21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a OR7D4 coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

Variants of OR7D4 include but are not limited to OR7D4 WM, OR7D4 P79L, OR7D4 D52G, OR7D4 S75C, OR7D4 M136I, OR7D4 L162P, OR7D4 A279D, OR7D4 L292M, OR7D4 H131Q, and OR7D4 C139Y (see, also, Table 1).

The present invention is not limited to particular uses of OR7D4 nucleic acids (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y). In some embodiments, OR7D4 nucleic acids are heterologously expressed in host cells to generate expressed OR7D4 proteins for purposes of characterizing protein function. In some embodiments, fragments of OR7D4 nucleic acids are used as diagnostic probes or primers. In some embodiments, fragments of OR7D4 nucleic acids are used for antisense/RNAi purposes.

II. OR7D4 Polypeptides

In other embodiments, the present invention provides OR7D4 polypeptide sequences (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4 H131Q, and OR7D4 C139Y) (e.g., the polypeptides of OR7D4 wild type, OR7D4 WM (R188W/T133M), OR7D4 P79L, and OR7D4 S84N respectively). In some embodiments, the present invention provides a polypeptide having an amino acid selected from one or more of OR7D4 wild type, OR7D4 WM (R188W/T133M), OR7D4 P79L, and OR7D4 S84N and variants thereof that are at least 80% identical to OR7D4 wild type, OR7D4 WM (R188W/T133M), OR7D4 P79L, and OR7D4 S84N. In some embodiments, the protein is at least 90% identical to OR7D4 wild type, OR7D4 WM (R188W/T133M), OR7D4 P79L, and OR7D4 S84N. In some embodiments, the protein is at least 95% identical to OR7D4 wild type, OR7D4 WM (R188W/T133M), OR7D4 P79L, and OR7D4 S84N. Other embodiments of the present invention provide fragments, fusion proteins or functional equivalents of OR7D4 proteins. In some embodiments, the present invention provides mutants of OR7D4 polypeptides (e.g., OR7D4 WM, OR7D4 P79L, OR7D4 D52G, OR7D4 S75C, OR7D4 M136I, OR7D4 L162P, OR7D4 A279D, OR7D4 L292M, OR7D4 H131Q, and OR7D4 C139Y, and functional equivalents). In some embodiments, the polypeptide may be a naturally purified product, in some embodiments it may be a product of chemical synthetic procedures, and in some embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In some embodiments, OR7D4 polypeptides (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y) display variant responses to odiferous agents (e.g., androstenone and androstadienone).

1. Vectors for Production of OR7D4 Polypeptides

The polynucleotides of the present invention may be employed for producing OR7D4 polypeptides by recombinant techniques. Thus, for example, the polynucleotide may be included in any one of a variety of expression vectors for expressing a OR7D4 polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., OR7D4 wild type, OR7D4 WM (R188W/T133M), OR7D4 P79L, and OR7D4 S84N). In some embodiments of the present invention, the constructs comprise a vector, such as a plasmid or viral vector, into which a sequence of the invention has been inserted, in a forward or reverse orientation. In still other embodiments, the heterologous structural sequence (e.g., OR7D4 wild type, OR7D4 WM (R188W/T133M), OR7D4 P79L, and OR7D4 S84N) is assembled in appropriate phase with translation initiation and termination sequences. In some embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the $E.$ $coli$ lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of genes in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in $E.$ $coli$).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 by that act on a promoter to increase its transcription. Enhancers useful in the present invention include, but are not limited to, the SV40 enhancer on the late side of the replication origin by 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of OR7D4 Polypeptides

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis,* and various species within the genera *Pseudomonas, Streptomyces,* and *Staphylococcus,* as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., [1989].

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

In some embodiments, the present invention provides a cell line (e.g., heterologous 293T cell line) comprising expression of odorant receptors (e.g., human odorant receptor, murine odorant receptor, synthetic odorant receptor) localized to the cell surface, REEP1, RTP1, RTP2, and $G_{\alpha olf}$ (see, e.g., U.S. Patent Application Publication No. 2006/0057640; herein incorporated by reference in its entirety). The cell line described in this embodiment is not limited to particular odorant receptors. In some embodiments, the odorant receptors expressed in the cell line include, but are not limited to, OR7D4 and variant forms, S6/79, S18, S46, S50, MOR23-1, MOR31-4, MOR31-6, MOR32-5 and MOR32-11. In some embodiments, the human odorant receptors include, but are not limited to, OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y. In some embodiments, the odorant receptor (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y) is tagged with a reporting agent (e.g., glutathione-S-transferase (GST), c-myc, 6-histidine (6×-His), green fluorescent protein (GFP), maltose binding protein (MBP), influenza A virus haemagglutinin (HA), b-galactosidase, and GAL4). In some embodiments, cell lines expressing odorant receptors are used in the classification of an odorant receptor's functional expression (e.g., ligand specificity). In even further embodiments, cell lines expressing odorant receptors are used in the classification of an animal's olfactory sensation.

3. Purification of OR7D4 Polypeptides

The present invention also provides methods for recovering and purifying OR7D4 polypeptides from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having a coding sequence of a OR7D4 gene (e.g., OR7D4 wild type, OR7D4 WM (R188W/T133M), OR7D4 P79L, and OR7D4 S84N) fused in frame to a marker sequence that allows for purification of the polypeptide of the present invention. A non-limiting example of a marker sequence is a hexa-histidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

4. Truncation Mutants of OR7D4 Polypeptides

In addition, the present invention provides fragments of OR7D4 polypeptides (i.e., truncation mutants). In some embodiments of the present invention, when expression of a portion of the OR7D4 protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751 [1987]) and *Salmonella typhimurium* and its in vitro activity has been demonstrated on recombinant proteins (Miller et al., Proc. Natl. Acad. Sci. USA 84:2718 [1990]). Therefore, removal of an N-terminal methionine, if desired, can be achieved either in vivo by expressing such recombinant polypeptides in a host which produces MAP (e.g., *E. coli* or CM89 or *S. cerivisiae*), or in vitro by use of purified MAP.

5. Fusion Proteins Containing OR7D4

The present invention also provides fusion proteins incorporating all or part of the OR7D4 polypeptides of the present invention (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y). Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a OR7D4 protein. In some embodiments of the present invention, the VP6 capsid protein of rotavirus is used as an immunologic carrier protein for portions of a OR7D4 polypeptide, either in the monomeric form or in the form of a viral particle. In other embodiments of the present invention, the nucleic acid sequences corresponding to the portion of a OR7D4 polypeptide against which antibodies are to be raised can be incorporated into a fusion gene construct which includes coding sequences for a late vaccinia virus structural protein to produce a set of recombinant viruses expressing fusion proteins comprising a portion of OR7D4 as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of a OR7D4 polypeptide and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of OR7D4 is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the OR7D4 proteins (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y) can also be expressed and presented by bacterial cells.

In addition to utilizing fusion proteins to enhance immunogenicity, it is widely appreciated that fusion proteins can also facilitate the expression of proteins, such as a OR7D4 protein of the present invention (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y). Accordingly, in some embodiments of the present invention, OR7D4 polypeptides can be generated as glutathione-S-transferase (i.e., GST fusion proteins). It is contemplated that such GST fusion proteins will enable easy purification of OR7D4 polypeptides, such as by the use of glutathione-derivatized matrices (See e.g., Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of a OR7D4 polypeptide, can allow purification of the expressed OR7D4 fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of OR7D4

Still other embodiments of the present invention provide mutant or variant forms of OR7D4 polypeptides (i.e., muteins). It is possible to modify the structure of a peptide having an activity of a OR7D4 polypeptide of the present invention (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y) for such purposes as enhancing therapeutic or prophylactic efficacy, disabling the protein, or stability (e.g., ex vivo shelf life, and/or resistance to proteolytic degradation in vivo). Such modified peptides are considered functional equivalents of peptides having an activity of the subject OR7D4 proteins as defined herein (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y). A modified peptide can be produced in which the amino acid sequence has been altered, such as by amino acid substitution, deletion, or addition.

Moreover, as described above, variant forms (e.g., mutants or polymorphic sequences) of the subject OR7D4 proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present OR7D4 proteins, as well as truncation mutants, and is especially useful for identifying potential variant sequences (i.e., mutants or polymorphic sequences) that are involved in neurological disorders (e.g., olfactory disorders) or resistance to neurological disorders. The purpose of screening such combinatorial libraries is to generate, for example, novel OR7D4 variants that can act as either agonists or antagonists, or alternatively, possess novel activities all together.

Therefore, in some embodiments of the present invention, OR7D4 variants are engineered by the present method to provide altered (e.g., increased or decreased) biological activity. In other embodiments of the present invention, combinatorially-derived variants are generated which have a selective potency relative to a naturally occurring OR7D4. Such proteins, when expressed from recombinant DNA constructs, can be used in gene therapy protocols.

Still other embodiments of the present invention provide OR7D4 variants that have intracellular half-lives dramatically different than the corresponding wild-type protein. For example, the altered protein can be rendered either more stable or less stable to proteolytic degradation or other cellular process that result in destruction of, or otherwise inactivate OR7D4 polypeptides. Such variants, and the genes which encode them, can be utilized to alter the location of OR7D4 expression by modulating the half-life of the protein. For instance, a short half-life can give rise to more transient OR7D4 biological effects and, when part of an inducible expression system, can allow tighter control of OR7D4 levels within the cell. As above, such proteins, and particularly their recombinant nucleic acid constructs, can be used in gene therapy protocols.

In still other embodiments of the present invention, OR7D4 variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of OR7D4 homologs, variants or other related proteins are aligned, preferably to promote the highest homology possible. Such a population of variants can include, for example, OR7D4 homologs from one or more species, or OR7D4 variants from the same species but which differ due to mutation or polymorphisms (e.g., OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y). Amino acids that appear at each position of the aligned sequences are selected to create a degenerate set of combinatorial sequences.

In some embodiments of the present invention, the combinatorial OR7D4 library is produced by way of a degenerate library of genes encoding a library of polypeptides which each include at least a portion of potential OR7D4 protein sequences. For example, a mixture of synthetic oligonucleotides can be enzymatically ligated into gene sequences such that the degenerate set of potential OR7D4 sequences are expressible as individual polypeptides, or alternatively, as a set of larger fusion proteins (e.g., for phage display) containing the set of OR7D4 sequences therein.

There are many ways by which the library of potential OR7D4 homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential OR7D4 sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the 3rd Cleveland Symposium on Macromolecules*, Elsevier, Amsterdam, pp 273-289 [1981]; Itakura et al., Annu Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386 [1980]; Roberts et al., Proc. Natl. Acad. Sci. USA 89:2429 [1992]; Devlin et al., Science 249: 404 [1990]; Cwirla et al., Proc. Natl. Acad. Sci. USA 87: 6378 [1990]; each of which is herein incorporated by reference; as well as U.S. Pat. Nos. 5,223,409, 5,198,346, and 5,096,815; each of which is incorporated herein by reference).

It is contemplated that the OR7D4 nucleic acids of the present invention (e.g., OR7D4 wild type, OR7D4 WM (R188W/T133M), OR7D4 P79L, and OR7D4 S84N, and fragments and variants thereof) can be utilized as starting nucleic acids for directed evolution. These techniques can be utilized to develop OR7D4 variants having desirable properties such as increased or decreased biological activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 [1996]; Leung et al., Technique, 1:11 [1989]; Eckert and Kunkel, PCR Methods Appl., 1:17-24 [1991]; Caldwell and Joyce, PCR Methods Appl., 2:28 [1992]; and Zhao and Arnold, Nuc. Acids. Res., 25:1307 [1997]). After mutagenesis, the resulting clones are selected for desirable activity (e.g., screened for OR7D4 activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370:324 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 [1994]; Stemmer, Proc. Natl. Acad. Sci. USA, 91:10747 [1994]; Crameri et al., Nat. Biotech., 14:315 [1996]; Zhang et al., Proc. Natl. Acad. Sci. USA, 94:4504 [1997]; and Crameri et al., Nat. Biotech., 15:436 [1997]). Variants produced by directed evolution can be screened for OR7D4 activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of OR7D4 homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of OR7D4 Polypeptides

In an alternate embodiment of the invention, the coding sequence of OR7D4 is synthesized, whole or in part, using chemical methods well known in the art (See e.g., Caruthers et al., Nucl. Acids Res. Symp. Ser., 7:215 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807 [1981]). In other embodiments of the present invention, the protein itself is produced using chemical methods to synthesize either an entire OR7D4 amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 [1995]) and automated synthesis may be achieved, for example, using ABI 431A Peptide Synthesizer (Perkin Elmer) in accordance with the instructions provided by the manufacturer. Additionally, the amino acid sequence of a OR7D4 polypeptide, or any part thereof, may be altered during direct synthesis and/or combined using chemical methods with other sequences to produce a variant polypeptide.

III. Detection of OR7D4 Alleles

In some embodiments, the present invention provides methods of detecting the presence of wild type or variant (e.g., mutant or polymorphic) OR7D4 nucleic acids or polypeptides (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y). The detection of mutant OR7D4 polypeptides finds use in the diagnosis of disease (e.g., olfactory disorder) or the characterization of olfactory sensation.

Accordingly, the present invention provides methods for determining whether a patient has an increased susceptibility to olfactory disorders by determining, directly or indirectly, whether the individual has a variant OR7D4 allele (e.g., OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y).

The present invention also provides kits for determining whether an individual contains a wild-type or variant (e.g., mutant or polymorphic) allele or polypeptide of OR7D4 (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y).

In some embodiments, the present invention provides methods of determining an individual's risk of developing an olfactory disorder (e.g., upper respiratory infections, tumors of the anterior cranial fossa, and Kallmann syndrome, Foster Kennedy syndrome, Parkinson's disease, Alzheimer's disease, Huntington chorea) based on the presence of one or more variant alleles of a OR7D4 gene. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of contacting an OR7D4 related olfactory disorder associated with a given polymorphism, as well as the sequences). In some embodiments, one of the computers stores application programs (e.g., for analyzing the results of detection assays). Results are then delivered to the user (e.g., via one of the computers or via the internet).

IV. Generation of OR7D4 Antibodies

The present invention provides isolated antibodies or antibody fragments (e.g., FAB fragments). Antibodies (e.g., monoclonal, polyclonal) (e.g., single chain) can be generated to allow for the detection of OR7D4 proteins (e.g., wild type or mutant) of the present invention (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y). The antibodies may be prepared using various immunogens. In one embodiment, the immunogen is a human OR7D4 peptide to generate antibodies that recognize human OR7D4. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

V. Gene Therapy Using OR7D4

The present invention also provides methods and compositions suitable for gene therapy to alter OR7D4 expression (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y), production, or function for research, generation of transgenic animals, and/or therapeutic applications. As described above, the present invention provides human OR7D4 genes (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y) and provides methods of obtaining OR7D4 genes from other species. Thus, the methods described below are generally applicable across many species. In some embodiments, it is contemplated that the gene therapy is performed by providing a subject with a wild-type allele of a OR7D4 gene (i.e., an allele that does not contain a OR7D4 disease allele (e.g., free of disease causing polymorphisms or mutations)). Subjects in need of such therapy are identified by the methods described above. In some embodiments, transient or stable therapeutic nucleic acids are used (e.g., antisense oligonucleotides, siRNAs) to reduce or prevent expression of mutant proteins. In other embodiments, genes are deleted to reduce or block desired olfactory senses.

VI. Transgenic Animals Expressing Exogenous OR7D4 Genes and Homologs, Mutants, and Variants Thereof The present invention contemplates the generation of transgenic animals comprising an exogenous OR7D4 gene or homologs, mutants, or variants thereof (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y). In some embodiments, the transgenic animal displays an altered phenotype as compared to wild-type animals. In some embodiments, the altered phenotype is the overexpression of mRNA for a OR7D4 gene as compared to wild-type levels of OR7D4 expression. In other embodiments, the altered phenotype is the decreased expression of mRNA for an endogenous OR7D4 gene as compared to wild-type levels of endogenous OR7D4 expression. In some embodiments, the transgenic animals comprise mutant alleles of OR7D4. Methods for analyzing the presence or absence of such phenotypes include Northern blotting, mRNA protection assays, and RT-PCR. In other embodiments, the transgenic mice have a knock out mutation of a OR7D4 gene. In some embodiments, the transgenic animals display an altered susceptibility to olfactory disorders (e.g., upper respiratory infections, tumors of the anterior cranial fossa, and Kallmann syndrome, Foster Kennedy syndrome, Parkinson's disease, Alzheimer's disease, Huntington chorea).

Such animals find use in research applications (e.g., identifying signaling pathways that a OR7D4 protein is involved in), as well as drug screening applications (e.g., to screen for drugs that prevent or treat olfactory disorders). For example, in some embodiments, test compounds (e.g., a drug that is suspected of being useful to treat an olfactory disorder) are administered to the transgenic animals and control animals with a wild type OR7D4 allele and the effects evaluated. The effects of the test and control compounds on disease symptoms are then assessed.

VII. Compound Screening Using OR7D4

In some embodiments, the isolated nucleic acid and polypeptides of OR7D4 genes of the present invention and related proteins and nucleic acids are used in drug screening applications for compounds that alter (e.g., enhance or inhibit) OR7D4 activity. The present invention further provides methods of identifying ligands of the OR7D4 proteins of the present invention.

The present invention is not limited to a particular mechanism. Indeed, an understanding of the mechanism is not necessary to practice the present invention. Nonetheless, based upon OR expression analysis experiments conducted during the course of the development of embodiments of the present invention, it is contemplated that OR7D4 family proteins function in olfactory sensation of steroids (e.g., androstenone and androstadienone). In some embodiments, the present invention provides methods of screening compounds for the ability to alter OR7D4 activity mediated by natural ligands (e.g., androstenone and androstadienone).

In some embodiments, the present invention provides methods of screening compounds for an ability to interact with mutant OR7D4 nucleic acid and/or mutant OR7D4 polypeptides, while simultaneously not interacting with wild type OR7D4 nucleic acid and/or wild type OR7D4 polypeptides. Such compounds find use in the treatment of olfactory disorders (e.g., altered olfactory sensation) facilitated by the presence of mutant forms of OR7D4 nucleic acids and/or proteins.

One technique uses antibodies capable of specifically binding to OR7D4 peptides and competing with a test compound for binding to OR7D4 peptides. Similar screens can be carried out with small molecule libraries, aptamers, etc.

The present invention contemplates the use of cell lines transfected with OR7D4 genes and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level.

In second messenger assays, the host cells are preferably transfected as described above with vectors encoding OR7D4 or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors or of ORs localized at the cell membrane. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DAB-CYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

The ability of a compound (e.g., an odiferous agent) to interact with OR7D4 with or without the labeling of any of the interactants can be evaluated. For example, a microphysiometer can be used to detect the interaction of a compound with OR7D4 without the labeling of either the compound or the OR7D4 (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and a OR7D4 polypeptide (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y).

In yet another embodiment, a cell-free assay is provided in which OR7D4 protein (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y) or biologically active portion thereof is contacted with a test compound and the ability of the test compound to bind to the OR7D4 protein or biologically active portion thereof is evaluated. Preferred biologically active portions of OR7D4 proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

VIII. Pharmaceutical Compositions Containing OR7D4 Nucleic Acid, Peptides, and Analogs The present invention further provides pharmaceutical compositions which may comprise all or portions of OR7D4 polynucleotide sequences, OR7D4 polypeptides, inhibitors or antagonists of OR7D4 bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by mutant OR7D4 alleles (e.g., upper respiratory infections, tumors of the anterior cranial fossa, and Kallmann syndrome, Foster Kennedy syndrome, Parkinson's disease, Alzheimer's disease, Huntington chorea). Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, OR7D4 nucleotide and OR7D4 amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, OR7D4 polynucleotide sequences or OR7D4 amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of OR7D4 may be that amount that suppresses olfactory disorder related symptoms. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of OR7D4, conditions indicated on the label may include treatment of condition related to olfactory disorders.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts OR7D4 levels.

A therapeutically effective dose refers to that amount of OR7D4 that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.01 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for OR7D4 than for the inhibitors of OR7D4. Administration to the bone marrow may necessitate delivery in a manner different from intravenous injections.

IX. RNA Interference (RNAi)

RNAi represents an evolutionary conserved cellular defense for controlling the expression of foreign genes in most eukaryotes, including humans. RNAi is triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001;15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing Brummelkamp et al, Science 2002; 296:550-3; and Holen et al, Nucleic Acids Res. 2002; 30:1757-66, both of which are herein incorporated by reference.

A. Designing and Testing RNAi for OR7D4

In order to design siRNAs for OR7D4 (e.g. that target OR7D4 mRNA) software design tools are available in the art (e.g. on the Internet). For example, Oligoengine's web page has one such design tool that finds RNAi candidates based on Elbashir's (Elbashir et al, Methods 2002; 26: 199-213, herein incorporated by reference) criteria. Other design tools may also be used, such as the Cenix Bioscience design tool offered by Ambion. In addition, there is also the Si2 silencing duplex offered by Oligoengine.

There are also RNA folding software programs available that allow one to determine if the mRNA has a tendency to fold on its own and form a "hair-pin" (which in the case of dsRNAi is not as desirable since one goal is to have the RNAi attach to the mRNA and not itself). One preferred configuration is an open configuration with three or less bonds. Generally, a positive delta G is desirable to show that it would not tend to fold on itself spontaneously.

siRNA candidate molecules that are generated can be, for example, screened in an animal model of an olfactory disorder for the quantitative evaluation of OR7D4 expression in vivo using similar techniques as described above.

B. Expression Cassettes

OR7D4 specific siRNAs of the present invention may be synthesized chemically. Chemical synthesis can be achieved by any method known or discovered in the art. Alternatively, OR7D4 specific siRNAs of the present invention may be synthesized by methods which comprise synthesis by transcription. In some embodiments, transcription is in vitro, as from a DNA template and bacteriophage RNA polymerase promoter, in other embodiments, synthesis is in vivo, as from a gene and a promoter. Separate-stranded duplex siRNA, where the two strands are synthesized separately and annealed, can also be synthesized chemically by any method known or discovered in the art. Alternatively, ds siRNA are synthesized by methods that comprise synthesis by transcription. In some embodiments, the two strands of the double-stranded region of a siRNA are expressed separately by two different expression cassettes, either in vitro (e.g., in a transcription system) or in vivo in a host cell, and then brought together to form a duplex.

Thus, in another aspect, the present invention provides a composition comprising an expression cassette comprising a promoter and a gene that encodes a siRNA specific for OR7D4. In some embodiments, the transcribed siRNA forms a single strand of a separate-stranded duplex (or double-stranded, or ds) siRNA of about 18 to 25 base pairs long; thus, formation of ds siRNA requires transcription of each of the two different strands of a ds siRNA. The term "gene" in the expression cassette refers to a nucleic acid sequence that comprises coding sequences necessary for the production of a siRNA. Thus, a gene includes but is not limited to coding sequences for a strand of a ds siRNA.

Generally, a DNA expression cassette comprises a chemically synthesized or recombinant DNA molecule containing at least one gene, or desired coding sequence for a single strand of a ds siRNA, and appropriate nucleic acid sequences necessary for the expression of the operably linked coding sequence, either in vitro or in vivo. Expression in vitro may include expression in transcription systems and in transcription/translation systems. Expression in vivo may include expression in a particular host cell and/or organism. Nucleic acid sequences necessary for expression in a prokaryotic cell or in a prokaryotic in vitro expression system are well known and usually include a promoter, an operator, and a ribosome binding site, often along with other sequences. Eukaryotic in vitro transcription systems and cells are known to utilize promoters, enhancers, and termination and polyadenylation signals. Nucleic acid sequences necessary for expression via bacterial RNA polymerases (such as T3, T7, and SP6), referred to as a transcription template in the art, include a template DNA strand which has a polymerase promoter region followed by the complement of the RNA sequence desired (or the coding sequence or gene for the siRNA). In order to create a transcription template, a complementary strand is annealed to the promoter portion of the template strand.

In any of the expression cassettes described above, the gene may encode a transcript that contains at least one cleavage site, such that when cleaved results in at least two cleavage products. Such products can include the two opposite strands of a ds siRNA. In an expression system for expression in a eukaryotic cell, the promoter may be constitutive or inducible; the promoter may also be tissue or organ specific (e.g. specific to the eye), or specific to a developmental phase. Preferably, the promoter is positioned 5' to the transcribed region. Other promoters are also contemplated; such promoters include other polymerase III promoters and microRNA promoters.

Preferably, a eukaryotic expression cassette further comprises a transcription termination signal suitable for use with the promoter; for example, when the promoter is recognized by RNA polymerase III, the termination signal is an RNA polymerase III termination signal. The cassette may also include sites for stable integration into a host cell genome.

C. Vectors

In other aspects of the present invention, the compositions comprise a vector comprising a gene encoding an siRNA specific for OR7D4 or preferably at least one expression cassette comprising a promoter and a gene which encodes a sequence necessary for the production of a siRNA specific for OR7D4 (an siRNA gene). The vectors may further comprise marker genes, reporter genes, selection genes, or genes of interest, such as experimental genes. Vectors of the present invention include cloning vectors and expression vectors. Expression vectors may be used in in vitro transcription/translation systems, as well as in in vivo in a host cell. Expression vectors used in vivo in a host cell may be transfected into a host cell, either transiently, or stably. Thus, a vector may also include sites for stable integration into a host cell genome.

In some embodiments, it is useful to clone a siRNA gene downstream of a bacteriophage RNA polymerase promoter into a multicopy plasmid. A variety of transcription vectors containing bacteriophage RNA polymerase promoters (such as T7 promoters) are available. Alternatively, DNA synthesis can be used to add a bacteriophage RNA polymerase promoter upstream of a siRNA coding sequence. The cloned plasmid DNA, linearized with a restriction enzyme, can then be used as a transcription template (See for example Milligan, J F and Uhlenbeck, OC (1989) Methods in Enzymology 180: 51-64).

In other embodiments of the present invention, vectors include, but are not limited to, chromosomal, nonchromosomal and synthetic DNA sequences (e.g., derivatives of viral DNA such as vaccinia, adenovirus, fowl pox virus, and pseudorabies). It is contemplated that any vector may be used as long as it is expressed in the appropriate system (either in vitro or in vivo) and viable in the host when used in vivo; these two criteria are sufficient for transient transfection. For stable transfection, the vector is also replicable in the host.

Large numbers of suitable vectors are known to those of skill in the art, and are commercially available. In some embodiments of the present invention, mammalian expression vectors comprise an origin of replication, suitable promoters and enhancers, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, a gene sequence in an expression vector which is not part of an expression cassette comprising a siRNA gene (specific for OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y) is operatively linked to an appropriate expression control sequence(s) (promoter) to direct mRNA synthesis. In some embodiments, the gene sequence is a marker gene or a selection gene. Promoters useful in the present invention include, but are not limited to, the cytomegalovirus (CMV) immediate early, herpes simplex virus (HSV) thymidine kinase, and mouse metallothionein promoters and other promoters known to control expression of gene in mammalian cells or their viruses. In other embodiments of the present invention, recombinant expression vectors include origins of replication and selectable markers permitting transformation of the host cell (e.g., dihydrofolate reductase or neomycin resistance for eukaryotic cell culture).

In some embodiments of the present invention, transcription of DNA encoding a gene is increased by inserting an enhancer sequence into the vector. Enhancers are cis-acting elements of DNA, usually about from 10 to 300 by that act on a promoter to increase its transcription. Enhancers useful in the present invention include, but are not limited to, a cytomegalovirus early promoter enhancer, the polyoma enhancer on the late side of the replication origin, and adenovirus enhancers.

Preferably the design of a vector is configured to deliver the RNAi for more permanent inhibition. For example the pSilencer siRNA expression vector offered by Ambion, the pSuper RNAi system offered by Oligoengine, and the GneSilencer System offered by IMGENEX. These are all plasmid vector based RNAis. BD Biosciences offer the RNAi-Ready pSIREN Vectors, that allow both a Plasmid-based vectors and an Adenoviral or a Retroviral delivery formats. Ambion is expected to release an adenoviral vector for siRNA shortly. For the design of a vector there is no limitation regarding the folding pattern since there is no concern regarding the formation of a hairpin or at least there are no studies that found any difference in performance related to the mRNA folding pattern. Therefore, OR7D4 wild type, OR7D4 WM (R188W/T133M), OR7D4 P79L, and OR7D4 S84N, for example, may be used with in a Vector (both Plasmid and Viral) delivery systems.

It is noted that Ambion offers a design tool for a vector on their web page, and BD Biosciences offers a manual for the design of a vector, both of which are useful for designing vectors for siRNA.

D. Transfecting cells

In yet other aspects, the present invention provides compositions comprising cells transfected by an expression cassette of the present invention as described above, or by a vector of the present invention, where the vector comprises an expression cassette (or simply the siRNA gene) of the present invention, as described above. In some embodiments of the present invention, the host cell is a mammalian cell. A transfected cell may be a cultured cell or a tissue, organ, or organismal cell. Specific examples of cultured host cells include, but are not limited to, Chinese hamster ovary (CHO) cells, COS-7 lines of monkey kidney fibroblasts, 293T, C127, 3T3, HeLa, and BHK cell lines. Specific examples of host cells in vivo include tumor tissue and eye tissue.

The cells may be transfected transiently or stably (e.g. DNA expressing the siRNA is stably integrated and expressed by the host cell's genome). The cells may also be transfected with an expression cassette of the present invention, or they are transfected with an expression vector of the present invention. In some embodiments, transfected cells are cultured mammalian cells, preferably human cells. In other embodiments, they are tissue, organ, or organismal cells.

In the present invention, cells to be transfected in vitro are typically cultured prior to transfection according to methods which are well known in the art, as for example by the preferred methods as defined by the American Tissue Culture Collection. In certain embodiments of the present invention, cells are transfected with siRNAs that are synthesized exogenously (or in vitro, as by chemical methods or in vitro transcription methods), or they are transfected with expression cassettes or vectors, which express siRNAs within the transfected cell.

In some embodiments, cells are transfected with siRNAs by any method known or discovered in the art which allows a cell to take up exogenous RNA and remain viable. Non-limiting examples include electroporation, microinjection, transduction, cell fusion, DEAE dextran, calcium phosphate precipitation, use of a gene gun, osmotic shock, temperature shock, and electroporation, and pressure treatment. In alternative, embodiments, the siRNAs are introduced in vivo by lipofection, as has been reported (as, for example, by Elbashir et al. (2001) Nature 411: 494-498, herein incorporated by reference).

In other embodiments expression cassettes or vectors comprising at least one expression cassette are introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al. (1992) J. Biol. Chem., 267: 963; Wu and Wu (1988) J. Biol. Chem., 263:14621; and Williams et al. (1991) Proc. Natl. Acad. Sci. USA 88:272). Receptor-mediated DNA delivery approaches are also used (Curiel et al. (1992) Hum. Gene Ther., 3:147; and Wu and Wu (1987) J. Biol. Chem., 262:4429). In some embodiments, various methods are used to enhance transfection of the cells. These methods include but are not limited to osmotic shock, temperature shock, and electroporation, and pressure treatment.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker. The use of cationic lipids may promote encapsulation of negatively charged nucleic acids, and also promote fusion with negatively charged cell membranes. Particularly useful lipid compounds and compositions for transfer of nucleic acids are described in WO95/18863 and WO96/17823, and in U.S. Pat. No. 5,459,127, herein incorporated by reference. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a sequence encoding a siRNA in vivo as a naked DNA, either as an expression cassette or as a vector. Methods for formulating and administering naked DNA to mammalian muscle tissue are disclosed in U.S. Pat. Nos. 5,580,859 and 5,589,466, both of which are herein incorporated by reference.

Stable transfection typically requires the presence of a selectable marker in the vector used for transfection. Transfected cells are then subjected to a selection procedure. Generally, selection involves growing the cells in a toxic substance, such as G418 or Hygromycin B, such that only those cells expressing a transfected marker gene conferring resistance to the toxic substance upon the transfected cell survive and grow. Such selection techniques are well known in the art. Typical selectable markers are well known, and include genes encoding resistance to G418 or hygromycin B.

In some embodiments, the transfecting agent is OLIGOFECTAMINE. OLIGOFECTAMINE is a lipid based transfection reagent. Additional example of lipid based transfection reagents that were designed for the transfection of dsRNAis are the Transit-TKO reagent which is provided by Minis (Madison, Wis.) and the jetSI which was introduced by Polyplus-trasfection SAS. In addition, the Silencer siRNA Transfection Kit provided by Ambion's includes siPORT Amine and siPORT Lipid transfection agents. Roche offers the Fugene 6 transfection reagents that are also lipid based. There is an option to use electroporation in cell culture. Preferably a plasmid vector delivery system is transfected into the cell with OLIGOFECTAMINE provided by Invitrogen or with siPORT XP-1 transfection agent provided by Ambion.

In certain embodiments, certain chemical modifications of the dsRNAis such as changing the lipophilicity of the molecule may be employed (e.g., attachment of lipophilic residues at the 3' termini of the dsRNA). Delivery of dsRNAs into organisms may also be achieved with methods previously developed for the application of antisense oligonucleotides such as injection of liposomes-encapsulated molecules.

E. Generating OR7D4 specific siRNA

The present invention also provides methods of synthesizing siRNAs specific for OR7D4 (e.g. human OR7D4) or specific for mutant or wild type forms of OR7D4 (e.g., OR7D4, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y). The siRNAs may be synthesized in vitro or in vivo. In vitro synthesis includes chemical synthesis and synthesis by in vitro transcription. In vitro transcription is achieved in a transcription system, as from a bacteriophage RNA polymerase, or in a transcription/translation system, as from a eukaryotic RNA polymerase. In vivo synthesis occurs in a transfected host cell.

The siRNAs synthesized in vitro, either chemically or by transcription, are used to transfect cells. Therefore, the present invention also provides methods of transfecting host cells with siRNAs synthesized in vitro; in particular embodiments, the siRNAs are synthesized by in vitro transcription. The present invention further provides methods of silencing the OR7D4 gene in vivo by transfecting cells with siRNAs synthesized in vitro. In other methods, the siRNAs is expressed in vitro in a transcription/translation system from an expression cassette or expression vector, along with an expression vector encoding and expressing a reporter gene.

The present invention also provides methods of expressing siRNAs in vivo by transfecting cells with expression cassettes or vectors which direct synthesis of siRNAs in vivo. The present invention also provides methods of silencing genes in vivo by transfecting cells with expression cassettes or vectors that direct synthesis of siRNAs in vivo.

XI. Consumer Applications

In some embodiments, the present invention provides consumer applications configured to modulate (e.g., enhance, diminish) olfactory receptor activity. In some embodiments, the consumer applications are configured to modulate (e.g., enhance, diminish) OR7D4 activity. The present invention is not limited to particular consumer applications. Examples of consumer applications include, but are not limited to, cosmetic applications (e.g., perfumes, colognes, deodorants, soaps, lotions, personal lubricants, shampoos, hair gels, etc.), medical applications (e.g., inhalants, topical medications, etc.), and domestic applications (e.g., aerosol sprays, pot pouri, room deodorizers, scented candles). In some embodiments, the consumer applications modulate olfactory activity (e.g., OR7D4 activity) with personal application agents.

The present invention is not limited to a particular type of personal application agent (e.g., perfumes, colognes, deodorants, soaps, lotions, personal lubricants, shampoos, hair gels, inhalants, topical medications, aerosol sprays, pot pouri, room deodorizers, scented candles, etc.). The personal application agents are not limited to a particular manner of modulating OR7D4 activity. In some embodiments, the personal application agents comprise one or more ligands known to modulate OR7D4 activity. In some embodiments, the personal application agent is designed to modulate the activity of a particular polymorphism of OR7D4 (e.g., OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y). In some embodiments, the personal application agents are designed to modulate the activity of wild type OR7D4 and polymorphisms of OR7D4. In some embodiments, the personal application agents modulate OR7D4 activity through use of ligands known to modulate OR7D4 activity. For example, in some embodiments, the personal application agents comprise steroid agents such as androstenone and androstadienone or analogues thereof. The present invention is not limited to particular types or kinds of steroid agents (e.g., naturally occurring steroids, synthetic steroids). In some embodiments the steroid agents include naturally occurring and/or synthetic androstenone and androstadienone or OR7D4 ligands or inhibitors identified in the screening methods described herein.

As cortisol levels in women smelling androstadienone are maintained at higher levels than in women not smelling androstadienone (see, e.g., Wyart, C., et al., J. Neuroscience 2007 27(6):1261-1265; herein incorporated by reference in its entirety), the personal application agents of the present invention may be used to increase cortisol expression in subjects. In some embdodiments, the personal application agents of the present invention may be used to increase female sex drive through enhancing of cortisol expression and OR7D4 activity. In some embodiments, the personal application agents can be used to increase a subject's desire to mate through modulation of the subject's OR7D4 activity.

In some embodiments, the present invention provides methods for developing personalized personal application agents (e.g., perfumes, colognes, deodorants, soaps, lotions, personal lubricants, shampoos, hair gels, inhalants, topical medications, aerosol sprays, pot pouri, room deodorizers, scented candles, etc.). In some embodiments, a subject's OR7D4 genotype is identified, and based on the subjects identified OR7D4 genotype, a personal application agent is developed comprising ligands of OR7D4 specific to the subject's OR7D4 genotype. For example, for subject's having wild type OR7D4, personal application agents may be developed comprising one or more ligands that modulate wild type OR7D4. For subject's having an OR7D4 polymorphism genotype (e.g., OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y), personal application agents may be developed comprising one or more ligands that modulate such an OR7D4 genotype. In some embodiments, a subject may develop a personal application agent that is specific for a different subject's OR7D4 genotype. In some embodiments, a subject may develop a personal application agent that is specific to that subject's OR7D4 genotype. In some embodiments, the personal application agent contains a plurality of different ligands so as to activate or inhibit a plurality of different OR7D4 types. The methods are not limited to a particular A search for polymorphisms in OR7D4 in existing SNP databases and our own sequencing efforts revealed 13 SNPs in this receptor (see, Table 1). Sequencing the coding region of OR7D4 in 412 participants revealed that two polymorphisms (OR7D4 R88W and OR7D4 T133M) occurred at a reasonable frequency (p=0.154) and were in complete linkage disequilibrium in this population ($r^2=1$, D'=1). These non-synonymous substitutions lead to two amino acid changes (R88W and T133M), and thus the two most common alleles of this receptor as OR7LM RT and OR7LM WM. The allele frequency of these genotypes and the prevalence by racial group are detailed in Table 1 and Table 3. The WM allele is underrepresented in African-American subjects and overrepresented in Caucasian subjects relative to the RT allele (p=0.0008; Fisher's exact test) (see Table 3).

TABLE 3

Single Nucleotide Polymorphisms in OR7D4 and their Distribution among 412 subjects.

| SNP | dbSNP ID | Chromosomal Position | AA change | Allele frequency | | Racial self-identification | | | | | |
|---|---|---|---|---|---|---|---|---|---|---|---|
| | | | | | | African-American | Asian | Caucasian | Do not wish to specify | Native American | Other** |
| refseq | | | | 649/824 | 0.788 | 25% | 8% | 44% | 3% | 1% | 19% |
| 1 | | 9186359 | D52G | 2/824 | 0.002 | 100% | 0% | 0% | 0% | 0% | 0% |
| 2 | rs5020281 | 9186290 | S76C | 0/824 | 0 | | | | | | |
| 3 | | 9186278 | P79L | 35/824 | 0.042 | 80% | 0% | 0% | 6% | 0% | 14% |
| 4 | rs5020280 | 9186263 | S84N | 10/824 | 0.012 | 50% | 0% | 10% | 0% | 0% | 40% |
| 5 | | 9186232 | R88W | 127/824 | 0.154 | 14% | 9% | 61% | 5% | 1% | 10% |
| 6 | rs5020279 | 9186121 | H131Q | 0/824 | 0 | | | | | | |
| 7 | rs5020278 | 9186116 | T133M | 127/824 | 0.154 | 14% | 9% | 61% | 5% | 1% | 10% |
| 8 | rs5020277 | 9166106 | M138I | 0/824 | 0 | | | | | | |
| 9 | rs5020276 | 9186099 | C139R | 0/824 | 0 | | | | | | |
| 10 | rs5020275 | 9186098 | C139Y | 0/824 | 0 | | | | | | |
| 11 | | 9186029 | L162P | 1/824 | 0.001 | 0% | 0% | 100% | 0% | 0% | 0% |
| 12 | | 9185678 | A279D | 0/824 | 0* | | | | | | |
| 13 | rs4984704 | 9185840 | L292M | 0/824 | 0 | | | | | | |

*one individual with this SNP was found but was not used for psychophysical analysis.
**Of 73 subjects who chose "Other" as a race category, 60% self-identified as Hispanic, 16% as mixed race, and 10% as African.

manner of obtaining a subject's OR7D4 genotype. In some embodiments, non-invasive techniques are used to identify a subject's OR7D4 genotype (e.g., hair sample, cheek swab, etc.). Such methods find use in a wide variety of settings including cosmetic research settings, medical research settings, and domestic research settings. In some embodiments, the methods are used to identify new polymorphisms of OR7D4.

EXAMPLES

Example 1

The hypothesis that polymorphisms in odorant receptors contribute to the variability in human odor perception was investigated by combining a cell-based assay technique to deorphanize odorant receptors (see, e.g., Saito, H., et al., Cell 119:679-691 (2004); herein incorporated by reference in its entirety) with an olfactory psychophysics study of a diverse population of human subjects (see, e.g., Keller, A., et al., Curr Biol 14, R875-878 (2004); herein incorporated by reference in its entirety). A panel of 337 human odorant receptors was cloned and expressed in Hana3A cells, an HEK293T-derived cell line stably expressing accessory factors for odorant receptor expression (see, e.g., Saito, H., et al., Cell 119:679-691 (2004); herein incorporated by reference in its entirety), and screened for androstenone-mediated stimulation. A single odorant receptor, OR7D4, showed robust responses to this ligand (see FIG. 1a).

Example II

Figure 1B:
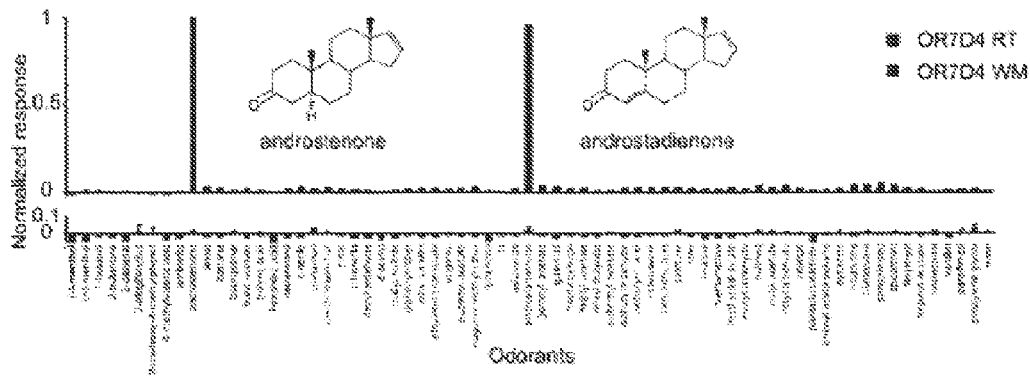
FIG. 1B, Specificity of OR7D4 RT tested against a panel of 66 odors and 2 solvents presented at 30 pM or 1,130,000 dilution. Only androstenone and androstadienone elicited a response. OR7D4 WM does not respond to any of the ligands tested. Y-axis denotes normalized response+SEM (n=4).
Figure 1C:
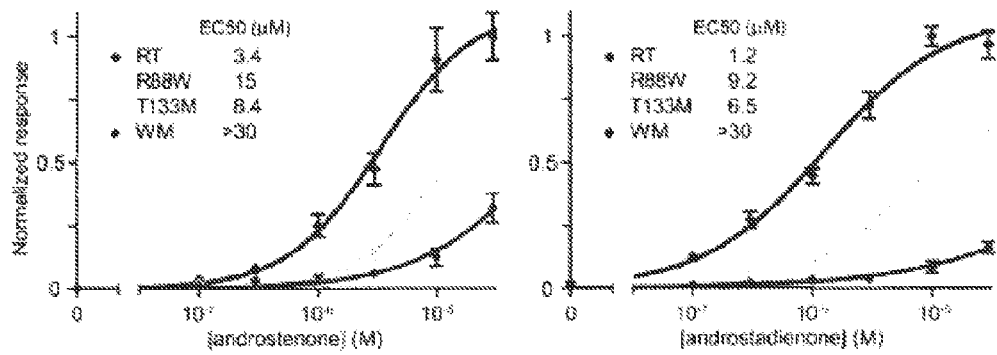
FIG. 1C, Dose response curves of OR7D4 RT, WM, R88W, and T133M for androstenone and androstadienone. EC50 values in pM are provided. Y-axis denotes normalized response±SEM (n=6).

The ligand specificity of both receptor variants in vitro was investigated against a panel of 66 odors and two solvents using a luciferase assay that converted odorant receptor activation to reporter gene activity. OR7D4 RT responded selectively to androstenone and the closely related odorous steroid, androstadienone, but showed no responses to any of the other 64 odors or two solvents (FIG. 1b, top). OR7D4 WM showed no response to any compound at the concentrations tested here (FIG. 1b, bottom). Dose response curves with OR7D4 RT and OR7D4 WM suggested that the paired SNPs in the WM variant severely impaired the function of this receptor (FIG. 1c). To investigate whether one or both of the variant residues caused this effect, ORs with each one of the SNPs were generated. OR7D4 R88W and OR7D4 T133M retained an intermediate level of function relative to OR7D4 RT indicating that both R88 and T133 residues contributed to the function of OR7D4 (FIG. 1c). OR7D4 is situated on chromosome 19 in a cluster of 8 odorant receptor genes and one pseudogene, which is adjacent and 92% identical to OR7D4. In the chimpanzee genome, the orthologue of OR7D4 and that of the linked pseudogene have intact open reading frames and the chimpanzee OR7D4 orthologue exists as the RT allele. The closest homologue to OR7D4 in the human genome is only 70% identical, indicating that this receptor is not part of a larger subfamily of closely related receptors.

Figure 2A:
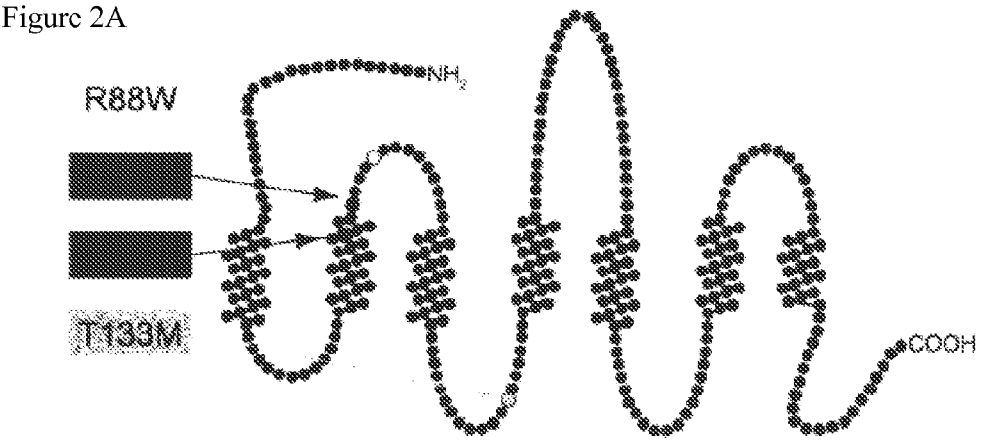
FIG. 2A, Sequence of OR7D4 represented as a snake plot, with the major non-synonymous SNPs and their corresponding amino acid changes indicated as coloured circles.
Figure 2B:
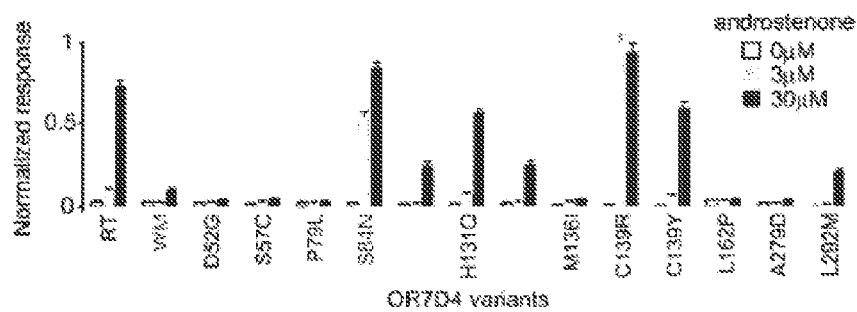
FIG. 2B, Characterization of receptor activity of 13 SNP variants in response to 3 pM and 30 pM androstenone in a luciferase assay. Y-axis denotes normalized response+SEM (n=4).

The non-synonymous substitutions in OR7D4 affects amino acids distributed throughout the protein (see, Table 1 and FIG. 2a). The function of the remaining 11 OR7D4 variants were tested in vitro and five additional variants with reduced function (OR7D4 D52G, OR7D4 S75C, OR7D4 P79L, OR7D4 M136I, OR7D4 L162P, OR7D4 A279D, and OR7D4 L292M) were identified, two variants that have similar level of function to the reference sequence (OR7D4H131Q and OR7D4 C139Y), and two variants that show increased function relative to OR7D4 RT (OR7D4 S84N and OR7D4 C139R) (FIG. 2b). Converse to the racial distribution of the WM allele, it was found that OR7D4 P79L and OR7D4 S84N were overrepresented in African-American relative to Caucasian subjects when compared to the RT allele (p=0.0001 and p=0.03, respectively; Fisher's exact test) (Table 3). Moreover, the SNPs OR7D4 S75C and OR7D4H131Q, OR7D4 W361, OR7D4 C139R, OR7D4 C139Y, OR7D4 and L292M did not appear in a rather large cohort of ethnically diverse individuals and represented either rare or not naturally occurring SNPs.

Example III

Figure 2C:
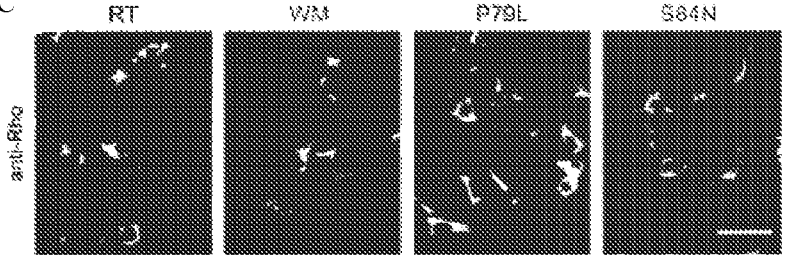
FIG. 2C, Permeabilized cell immunofluorescence of Hana3A cells expressing OR7D4 RT, WM, P79L, and S84N. Cells were stained with antirhodopsin antibody. Scale bar=50 pm.
Figure 2D:
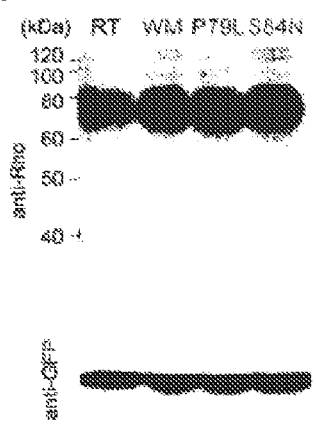
FIG. 2D, Western blot analysis of whole-cell lysates from HEK293T cells transfected with OR7D4 RT, WM, P79L, and S84N and GFP co-transfected as a control.
Figure 2E:
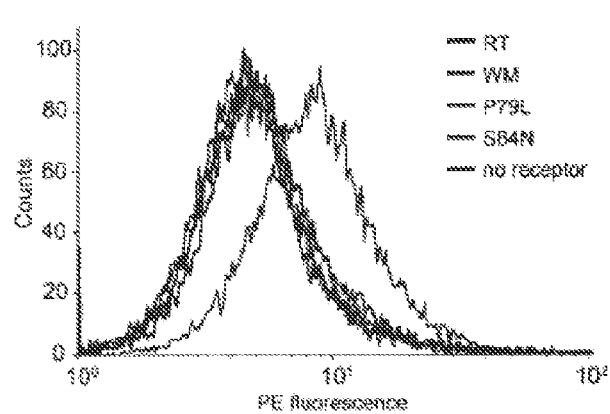
FIG. 2E, Flow cytometry analysis of the cell-surface expression of OR7D4 RT, WM, P79L, and S84N, co-expressed with GFP. The intensity of phycoerythrin (PE) signal among the GFP-positive population was measured and plotted.

This example describes the mechanism by which OR7D4 polymorphisms affect receptor function. The subcellular distribution, expression levels, and cell-surface distribution of the four major variants of OR7D4 (e.g., OR7D4 RT, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y) in Hana3A cells with an antibody that recognized the N-terminal epitope tag of the OR7D4 variants. Immunofluorescence staining of OR7D4 RT, OR7D4 WM, OR7D4 P79L, OR7D4 D52G, OR7D4 S75C, OR7D4 M136I, OR7D4 L162P, OR7D4 A279D, OR7D4 L292M, OR7D4H131Q, and OR7D4 C139Y proteins in permeabilized cells revealed no difference in subcellular distribution or expression level (FIG. 2c). Western blot analysis confirmed that all were expressed at comparable levels (FIG. 2d). Next, differences in cell surface expression were investigated to account for the functional differences between the variants. Flow cytometly analysis of live cells showed that OR7D4 RT, OR7D4 WM, and OR7D4 P79L had similar low levels of surface staining, while the OR7D4 S84N variant showed considerably more surface expression (FIG. 2e). These results indicated that, for example, SNPs in the OR7D4 WM and OR7D4 P79L alleles affected function by interfering with cell surface expression, ligand binding, signal transduction, or yet another mechanism, while the increased function of the OR7D4 S84N variant stemmed from enhanced stability or cell surface trafficking Example IV Whether variation in OR7D4 correlated with variation in the perception of androstenone and androstadienone measured in 412 subjects was next investigated. The common functional genotype (OR7D4 RT/RT) was found in 62% (N=255) of these subjects, the OR7D4 WM/WM genotype was found in 2% (N=10) of the subjects, and 24% (N=100) of the subjects had the heterozygous OR7D4 RT/WM genotype. The OR7D4 RT/P79L and RT/S84N genotypes were each found in ~2% of the subjects (N=10 and N=7, respectively) and 2% (N=10) subjects had various combinations of these and rarer SNPs (Table 1 and Table 3). Extensive psychophysical data were collected on all 412 subjects over the course of a two-year study that involved three different tasks: subjects rated the perceived intensity and valence (pleasantness or unpleasantness) of 66 different odors at two concentrations; detection thresholds were measured to androstenone and androstadienone in a subset of subjects and three control odors in all subjects (see, e.g., Doty, R. L., et al., Chem Senses 20, 645-656 (1995); Doty, R. L. & Laing, D. G. in Handbook of Olfaction and Gustation (ed. Doty, R. L.) pp. 203-228 (Marcel Dekker, Inc., New York, 2003); each herein incorporated by reference in their entireties); subjects profiled five odors with 146 semantic labels (see, e.g., Keller, A., et al., Curr Biol 14, R875-878 (2004); Dravnieks, A., et al., Science 218, 799-801 (1982); each of which are herein incorporated by reference in their entireties). Psychophysical data were subsequently divided according to genotype and assessed for the influence of OR7D4 genotype on perceptual phenotype. Rigorous statistical analysis, with Bonferroni correction for multiple comparisons, was imposed to establish the significance of the findings.

Figure 3A:
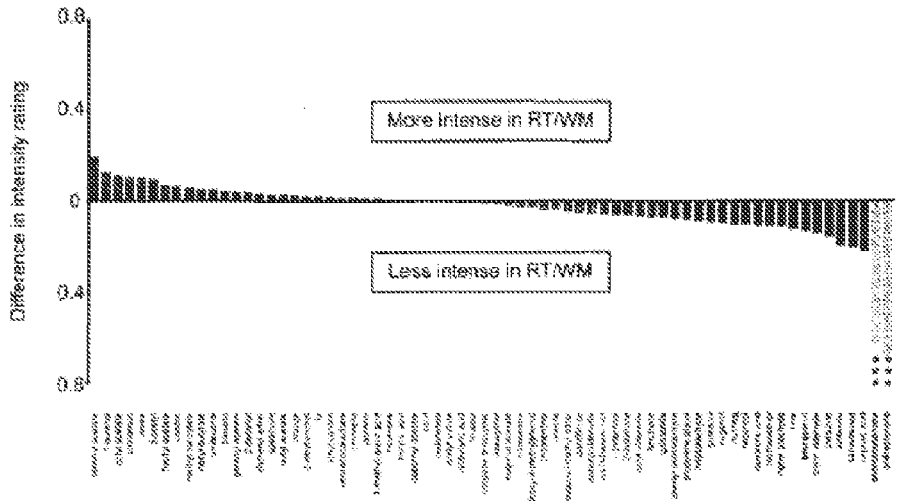
FIG. 3A, Mean differences in intensity rating for androstadienone and androstenone are significantly reduced in OR7D4 RTMM relative to OR7D4 RT/RT subjects from a panel of 66 odors and 2 solvents. The data for the two different concentrations of each dour are pooled.
Figure 3B:
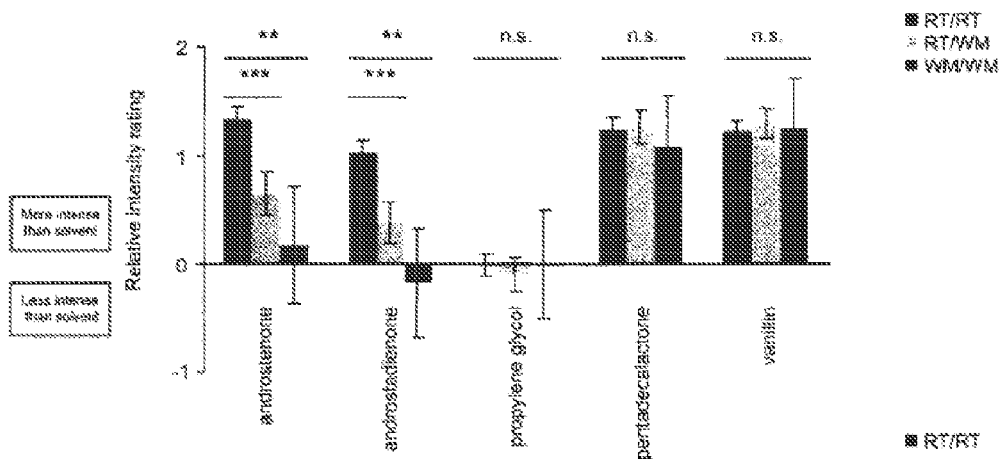
FIG. 3 shows OR7D4 WM correlates with reduced intensity perception of androstenone and androstadienone.
FIG. 3C, Detection thresholds for androstenone plotted as percent of subjects detecting this dour at a given binary dilution.
FIG. 3D, Detection thresholds for androstadienone plotted as percent of subjects detecting this odor at a given binary dilution. Significance in a and b was assessed with Student's t-test with a Bonferroni correction ($p<0.01$; *$p<0.001$). Significance in c and d was assessed with the Kolmogorov-Smirnov test (*$p<0.05$). Number of subjects tested in (a) and (b) was N=255 RT/RT, N=100 RT/WM, and N=10 WM/WM subjects and in (c) and (d) was N=47 RT/RT, N=49 RT/wWM.

How the OR7D4 WM allele affected androstenone and androstadienone odor intensity perception was first investigated. Of the 66 odors and two solvents rated by all OR7D4 RT/RT and RT/WM subjects, only androstenone and androstadienone showed a significant effect of genotype (FIG. 3a). These steroids were rated as less intense by OR7D4 RT/WM subjects (FIG. 3a). This phenotype was specific for these two compounds, as the perception of other similar steroidal and musky compounds such as pentadecalactone, ambrette, and galaxolide was not affected by OR7D4 genotype (FIG. 3a-b). The reduction in androstenone and androstadienone odor intensity was more marked in the few OR7D4 WM/WM subjects screened (FIG. 3b). Therefore, the reduced function of the OR7D4 WM variant measured in vitro (see, FIG. 1b) correlated with reduced perception of the OR7D4 ligands in vivo. The present invention is not limited to a particular mechanism. Indeed, an understanding of the mechanism is not necessary to practice the present invention. Nonetheless, based upon theses results, it is likely that RT/WM heterozygous subjects have 50% fewer olfactory neurons expressing a functional OR7D4 variant, thus explaining the reduced sensitivity to androstenone and androstadienone.

Figure 3C:
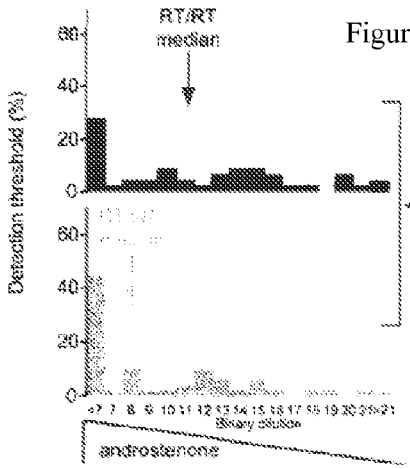
Figure 3D:
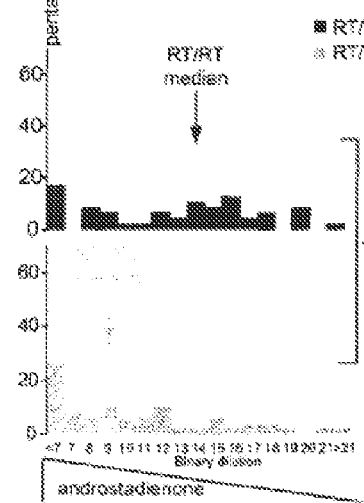

Detection thresholds of a subset of the subjects were determined for both steroidal odors (FIG. 3c). It was found that OR7D4 RT/WM subjects as a group had higher detection thresholds to both compounds (FIG. 3c) and a greater incidence of specific anosmia to androstenone than RT/RT subjects (p<0.05; chi-square test). The present invention is not limited to a particular mechanism. Indeed, an understanding of the mechanism is not necessary to practice the present invention. Nonetheless, these results indicate that the OR7D4 WM allele affects human sensitivity to androstenone and androstadienone.

Example V

Figure 4A:
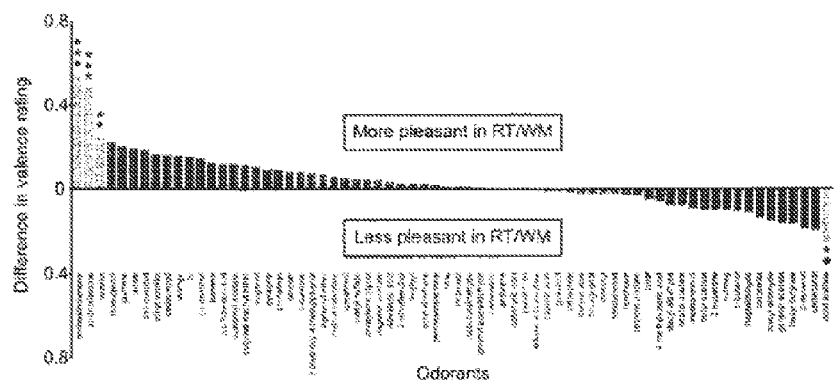
FIG. 4A, Mean differences in valence rating for androstadienone and androstenone are significantly increased in OR7D4 RTMM relative to OR7D4 RT/RT subjects from a panel of 68 odors and 2 solvents. The data for the two different concentrations of each dour are pooled.
Figure 4B:
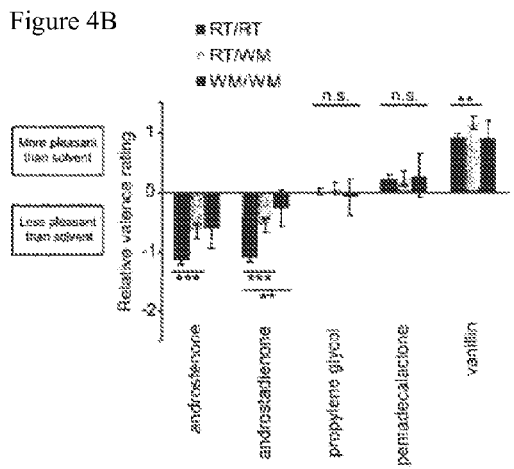
FIG. 4B, Relative valence ratings for five odors from a for OR7D4 RT/RT, RT/WM, and WM/WM subjects compared to solvent (propylene glycol). Ratings that are less pleasant than the solvent are negative in this figure. Mean±S.E.M.
Figure 4C:
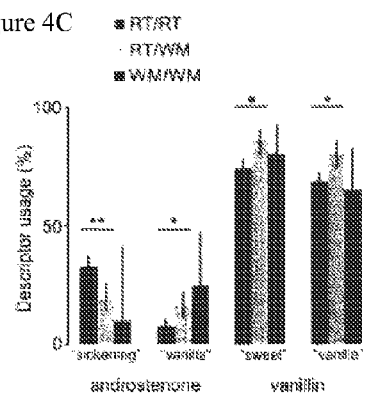
FIG. 4C, Odor profiling of androstenone, vanillin, pentadecalactone, and solvent (propylene glycol) by OR7D4 RT/RT, RT/WM, and WM/WM subjects show that RT/WM subjects differ in their usage of 2/146 descriptors for androstenone and vanillin. Data are plotted as % of individual sessions in which a given descriptor was used for an odor, with 95% confidence intervals represented as black lines. Significance in a and b was assessed with Student's t-test with a Bonferroni correction (*$p<0.05$; $p<0.01$; *$p<0.001$). Significance in c was assessed with a chi-square test with Bonferroni correction (*$p<0.05$). Number of subjects tested was N=255 RT/RT, N=100 RT/wWM, and N=10 WM/WM subjects.

After establishing that the OR7D4 WM polymorphism affects sensitivity, the perception of androstenone and androstadienone odor quality was investigated. OR7D4 RT/WM subjects rated both steroidal odors as more pleasant than OR7D4 RT/RT subjects (FIG. 4). This change in odor quality perception was largest for the steroids although a less pronounced—but statistically significant—difference was found for vanillin and octyl acetate (FIG. 4b). OR7D4 WM/WM subjects as a group were not anosmic to both steroidal compounds as they rated these as more unpleasant than the solvent, propylene glycol (FIG. 4b). Subjects rated androstenone odor quality by profiling this odor with a standard set of 146 semantic labels (see, e.g., Keller, A., et al., Curr Biol 14, R875-878 (2004); Dravnieks, A., et al., Science 218,799-801 (1982); each of which are herein incorporated by reference in their entireties). All descriptors used by more than 10% of subjects were analyzed and the usage of individuals with differing genotypes was compared. Of the 74 such descriptors used for androstenone, vanillin and the solvent, propylene glycol, only four differed significantly by genotype (see Supplementary Methods for details). OR7D4 RT/WM subjects were less likely to consider androstenone "sickening" and more likely to rate it as smelling like "vanilla" than RT/RT subjects (FIG. 4c). These same subjects showed a comparable increase in their use of two descriptors for the dour vanillin (FIG. 4c).

Figure 5A:
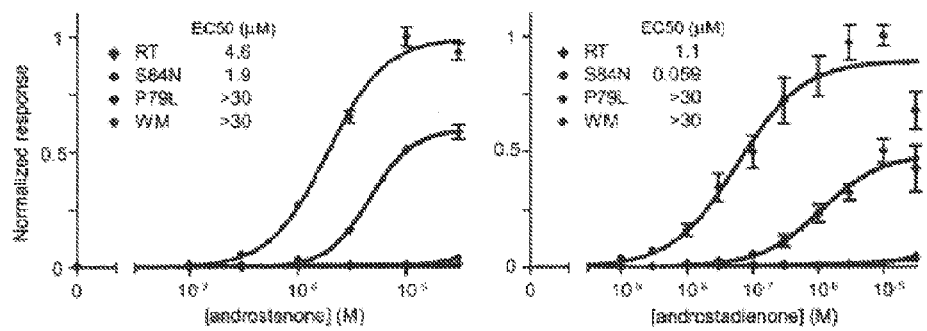
FIG. 5A, Dose response curves of OR7D4 RT, WM, P79L, and S84N for androstenone and androstadienone. EC50 values in μM are provided. Y-axis denotes normalized response±SEM (n=6 for androstenone and n=4 for androstadienone).
Figure 5B:
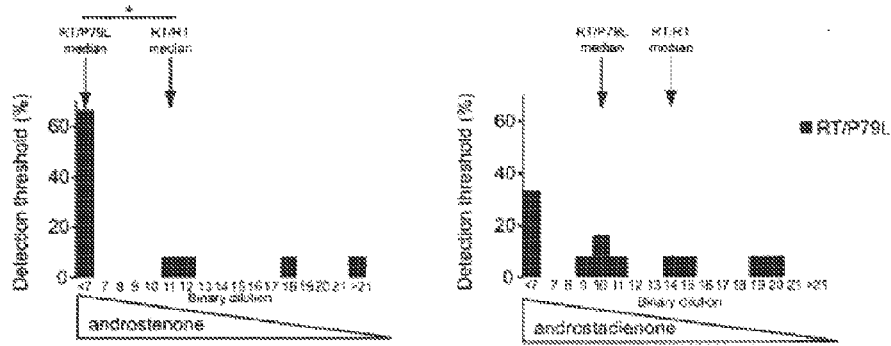
FIG. 5B, Detection thresholds for androstenone and androstadienone in OR7D4 RT/P79L subjects plotted as percent of subjects detecting these odors at a given binary dilution. Significance in was assessed with the Kolmogorov-Smirnov test (*$p<0.05$) N=12 subjects.
Figure 5C:
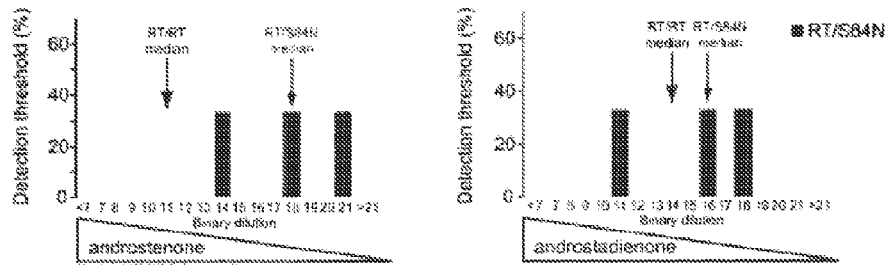
FIG. 5C, Detection thresholds for androstenone and androstadienone in OR7D4 RT/S84N subjects plotted as percent of subjects detecting these odors at a given binary dilution. N=3 subjects.
Figure 6A:
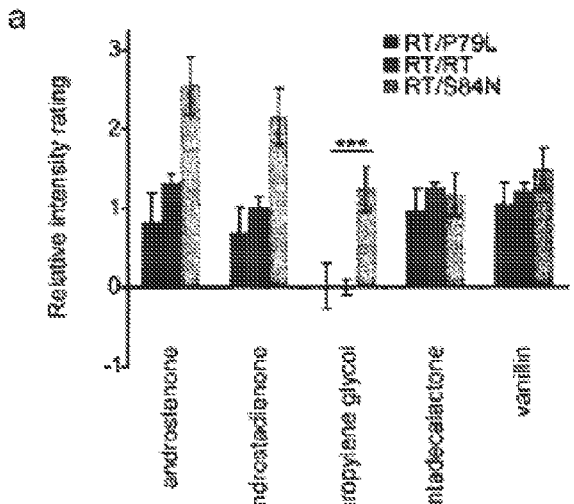
FIG. 6A, Intensity rating of RT/P79L (N=30) and RT/S84N(N=7) subjects compared to RT/RT subjects (N=255).
Figure 6B:
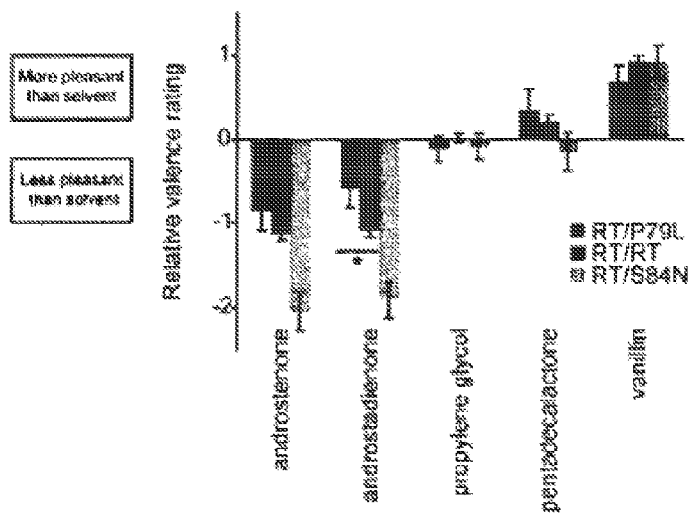
FIG. 6B, Valence rating of RT/P79L (N=30) and RT/S84N(N=7) subjects in comparison to RT/RT subjects (N=256). Mean±S.E.M. is plotted. There is a trend for RT/P79L subjects to perceive androstenone and androstadienone as less intense and more pleasant than the RT/RT subjects and for RT/S84N to perceive androstenone and androstadienone as more intense and less pleasant than the RT/RT subjects. This is consistent with the in vitro findings and the thresholds. Significance in was assessed with Student's t-test with a Bonferroni correction (*$p<0.05$; ***$p<0.001$).

To extend the observation that OR7D4 variation affects the perception of androstenone and androstadienone, the severely impaired OR7D4 P79L variant and the variant with increased function, OR7D4 S84N were examined. Dose-response analysis of OR7D4 P79L function in vitro showed severely impaired function at all concentrations of either steroidal odor tested (FIG. 5a). In contrast, OR7D4 S84N showed remarkable sensitivity to both odors in vitro, exceeding the activity of the common functional RT variant at every concentration tested, with an EC50 value to androstadienone nearly 20 times lower than the RT variant (FIG. 5a). Psychophysical analysis of subjects carrying RT/P79L and RT/S84N genotypes was consistent with the in vitro results, although statistical analysis was constrained by the small number of such individuals in the study group. It was found that RT/P79L subjects rated both androstenone and androstadienone as less intense and more pleasant than RT/RT controls (FIG. 6), and that these comparisons were significant for the androstadienone valence rating (FIG. 6b). Conversely, RT/S84N subjects rated both androstenone and androstadienone as more intense and less pleasant than RT/Rt controls (FIG. 6). Detection thresholds of a subset of RT/P79L and RT/S84N subjects to both odorous steroids were also obtained (FIG. 5b-c). The detection threshold of RT/P79L subjects to both androstenone and androstadienone was lower than RT/RT subjects (FIG. 5b), as was the proportion of subjects anosmic to androstenone (p=0.018; chi-square analysis). The detection threshold of RT/S84N subjects to both steroids was higher than RT/RT controls. Increased sensitivity to select musk compounds has been previously observed, suggesting that this type of specific hyperosmia may be a general phenomenon (see, e.g., Gilbert, A. N., et al., Chem Senses 21, 411416 (1996); herein incorporated by reference in its entirety). The present invention is not limited to a particular mechanism. Indeed, an understanding of the mechanism is not necessary to practice the present invention. Nonetheless, these results showed that genetic variation in OR7D4 correlated with variation in the perception of two sex steroid derived odors.

Example VI

This example describes the materials and methods used for Examples I-V.

Heterologous expression of human odorant receptors. 423 human odorant receptors including 337 predicted functional receptors were cloned. Odorant receptors that contained the first 20 amino acid of human rhodopsin (see, e.g., Krautwurst, D., et al., Cell 95, 917-926 (1998); herein incorporated by reference in its entirety) in pCl (Promega) were expressed in the Hana3A cell line along with a short form of mRTP1, RTP1S, (M37 to the C-terminal end), which enhanced functional expression of the odorant receptors. For immunocytochemistry, cells were fixed, permeabilized and incubated with monoclonal anti-rhodopsin antibody, 4D2 (see, e.g., Laird, D. W., et al., Invest Opthalmol Vis Sci 29.419428 (1988); herein incorporated by reference in its entirety), followed by Cy3-conjugated donkey anti-mouse IgG (Jackson Immunologicals). For FACS analysis, PE-conjugated donkey anti-mouse IgG (Jackson Immunologicals) was used. Western blot analysis was performed according to Mini-Protean 2 Cell (Bio-Rad) protocol. ECL (Amersham) was used for detecting proteins on membranes. After the initial exposure, the membrane was incubated with stripping buffer (25 mM Glycine-HCl [pH2], 1% SDS, 25 mM Glycine, 0.036N HCl, 1% SDS) and incubated with rabbit anti-GFP (Invitrogen). Luciferase assays were performed as described (see, e.g., Saito, H., et al., Cell 119:679-691 (2004); incorporated herein by reference in its entirety). All odors were supplied by Sigma-Aldrich at high purity, with these exceptions: androstadienone (a gift of Human Pheromone Sciences, Inc., Fremont, Calif.); banana (Bell Flavors and Fragrances); bourgeonal (Biomol); galaxolide (a gift of International Flavors and Fragrances); and r-carvone (Research Chemical Ltd.). The same batch and lot of each dour was used for both cell-based analysis and human olfactory psychophysics.

Human odorant receptor genotyping and sequencing. Venous blood was collected from all subjects and genomic DNA prepared with the Qiagen PAXgene blood DNA kit. Polymorphisms in OR7D4 were assayed by sequencing and allele-specific polymerase chain reaction (PCR). For sequencing, human genomic DNAs were amplified, purified, and sequenced with a 3100 or 3730 Genetic Analyzer (ABI Biosystems) or by GeneWiz (North Bmnswick, N.J.).

Human olfactory psychophysics. All human subjects gave informed consent to participate in this study and were tested in a well-ventilated room. Normal human subjects (n=412; 218 female, 194 male; median age 34, age range 19-75) were pre-screened to exclude pregnant women and those with medical conditions causing general impairment of the sense of smell. All subjects completed two replicates of the test separated by at least 4 days. Odors were presented in amber vials as previously described (see, e.g., Keller, A., et al., Nat Neurosci 7, 337-338 (2004); herein incorporated by reference in its entirety) using bar-coded symbols to ensure that subjects were blind to the identity of all odors. The intensity and valence of 66 odors at two concentrations ("high" and "low") and two solvents was rated using a 7-point scale. Thresholds were calculated using the single staircase method with seven reversals (see, e.g., Doty, R. L., et al., Chem Senses 20, 645-656 (1995); Doty, R. L. & Laing, D. G. in Handbook of Olfaction and Gustation (ed. Doty, R. L.) pp. 203-228 (Marcel Dekker, Inc., New York, 2003); each of which are herein incorporated by reference in their entireties). Threshold tests included both steroids as binary dilutions from 164 (binary dilution 6) to 1: 134,217,728 (binary dilution 27). Subjects who could not reliably distinguish a 1:64 dilution of androstenone and androstadienone from solvent were operationally defined as anosmic to these odorous steroids, although it could not be excluded that these subjects could detect higher concentrations of these steroids (see, e.g., Bremner, E. A., et al., Chem Senses 28, 423-432 (2003); herein incorporated by reference in its entirety). Odor profiling used the method established by Dravnieks, et al. (see, e.g., Dravnieks, A., et al., Science 218, 799-801 (1982); herein incorporated by reference in its entirety).

Cloning of human odorant receptors. 423 human odorant receptors were cloned with sequence information from The Olfactory Receptor Database (see, e.g., http:// followed by www. followed by senselab .med.yale.edu/senselab/ORDB/ default.asp). Of these, 337 were predicted to encode functional receptors, 45 were predicted to encode pseudogenes, 27 were variant pairs of the same genes, and 14 were duplicates. SNPs in OR7D4 were identified from the NCBI dbSNP database (see, e.g., http:// followed by www. followed by ncbi.nlm.nih.gov/projects/SNP) or through genotyping. OR7D4 single nucleotide variants were generated by overlap extension PCR.

Cell culture, immunocytochemistry, and flow cytometry. Odorant receptors that contained the first 20 amino acid of human rhodopsin tag in pCl (Promega) were expressed in the Hana3A cell line along with a short form of mRTP1, RTP1S, (M37 to the C-terminal end), which enhanced functional expression of the odorant receptors. For immunocytochemistry, cells were seeded in a 35 mm dish (Falcon) containing a piece of cover glass coated with poly-D-lysine (Sigma) 24 hrs prior to transfection in M10. Lipofectamine-2000 (Invitrogen) was used for transfection of plasmid DNA. Blue fluorescent protein (BFP) was cotransfected as a control for transfection efficiency. For live cell-surface staining, typically 24 hrs post-transfection, cells were incubated in MI0 containing mouse monoclonal anti-rhodopsin antibody, 4D2 (see, e.g., Bremner, E. A., et al., Chem Senses 28, 423-432 (2003); herein incorporated by reference in its entirety), 15 mM $NaN_3$, and 10 mM HEPES at 4° C. for 45 min. Cells were then washed in Hank's Balanced Buffer Solution (Gibco)15 mM $NaN_3$ and 10 mM HEPES, followed by incubation with Cy3-conjugated donkey anti-mouse IgG (Jackson Immunologicals) at 4° C. for 30 min and then fixation in 1% PFA at 4° C. and mounting in Mowiol. For permeabilized staining, 24 hrs posttransfection, cells were fixed in 4% PFA for 15 min and permeabilized with methanol at 4° C. Cells were blocked in 5% skim milk diluted in PBS, incubated in 5% skim milk/PBS containing mouse monoclonal anti-rhodopsin antibody, 4D2, at room temperature for 45 min. Cells were then washed in PBS followed by incubation with Cy3-conjugated donkey anti-mouse IgG (Jackson Immunologicals) at RT for 30 min. For FACS analysis, Hana3A cells were seeded in 35 mm dishes. At the time of transfection, green fluorescent protein (GFP) expression vector was co-transfected as a control for transfection efficiency. 24 hrs post-transfection, cells were incubated with 4D2 and then washed and incubated with PE-conjugated donkey anti-mouse IgG (Jackson Immunologicals). 7-amino-actinomycin D (Calbiochem) was added before flow cytometry to eliminate dead cells from analysis. The intensity of PE signal among the GFP-positive population was measured and plotted.

Western blot analysis. Hana3A cells in 35 mm dishes were transfected with Rho-tagged receptor variants and RTP1S using Lipofectamine-2000 (Invitrogen). GFP expression vector was cotransfected as a control. 24 hrs post-transfection, cells were lysed with sample loading buffer (20 mM Tris [pH 7.5], 2 mM EDTA, 5% SDS, 20% glycerol, 0.002% BPB, 0.25M DTT) and sonicated. SDS-PAGE and Western blot analysis were performed according to Mini-Protean 2 Cell (Bio-Rad) protocol. Membranes were incubated with 4D2 and subsequently with donkey anti-mouse HRP (Jackson Immunologicals). The membrane was then incubated with stripping buffer (25 mM Glycine-HCl [pH2], 1% SDS, 25 mM Glycine, 0.036N HCl, 1% SDS) for 30 min at room temperature and then with rabbit anti-GFP and subsequently with donkey anti-rabbit HRP. ECL (Amersham) was used for detecting proteins on membranes.

Luciferase assay and data analysis. Dual-Glo™ Luciferase Assay System (Promega) was used for luciferase assay as previously described (see, e.g., Whissell-Buechy, D., et al., Nature 242, 271-273 (1973); herein incorporated by reference in its entirety). CRE-luciferase (Stratagene) was used to measure receptor activation. *Renilla* luciferase driven by a constitutively active SV40 promoter (pRL-SV40; Promega) was used as an internal control for cell viability and transfection efficiency. Hana3A cells were plated on poly-D-lysine-coated 96-well plates (BioCoat; Becton Dickinson). Plasmid DNA of the receptor variants and RTP1S was transfected using Lipofectamine-2000. ~24 hrs post-transfection, the medium was replaced with CD293 chemically defined medium (Gibco) and then incubated for 30 min at 37T. The medium was then replaced with 254, of odorant solution diluted in CD293 and incubated for 4 hrs at 37° C. The manufacturer's protocols for measuring luciferase and *Renilla* luciferase activities were followed. Luminescence was measured using Wallac Victor 1420 (Perkin-Elmer). Normalized luciferase activity was calculated by the formula [luc(N)-luc(lowest)]/luc(highest)/RL (N) where luc(N)=luminescence of luciferase of a certain well; luc(lowest)=lowest luminescence of luciferase of a plate or a set of plates; luc(highest)=highest luminescence of luciferase of a plate or a set of plates; RL(N)=luminescence of *Renilla* luciferase of a certain well. Data was analyzed with Microsoft Excel and GraphPad Prism 4.

Human odorant receptor genotyping and sequencing. Venous blood was collected from all subjects and genomic DNA prepared with the Qiagen PAXgene blood DNA kit. Polymorphisms in OR7D4 were assayed by both sequencing and allele-specific PCR. In allele-specific PCR, an OR7D4 RT and an OR7D4 WM PCR were performed on each genomic DNA sample, each using a pair of internal primers containing the residues of interest. The RT forward primer is specific for R88 (5'-CTAGTGAGCATCCAGGCAC-3') and reverse primer is specific for T133 (5'-CAGGGGTTCAT-GATGACCG-3'). The WM forward primer contains W88 (5'-CTAGTGAGCATCCAGGCAT-3') and the reverse primer contains M133 (5'-CAGGGG'M'CATGATGACCA-3'). The PCR was done using HotStar Taq (Qiagen). Cycling protocol was: 95° C., 15 min; 30 cycles of 95° C., 15 sec; 66° C., 30s; 72° C., 1 min; and then 72° C., 10 min. Fifty percent of each reaction was analyzed on a 1% agarose gel (Research Products International Corp.). For sequencing, human genomic DNAs were PCRed with HotStar Taq (Qiagen) with primers upstream (5'-AAGTGATGACAAGCTGAGCTGC-3') and downstream (5'-CCACAACATITGCCTTAGGGGTA-3') of the OR7D4 open reading frame. The PCR products were then either gel-purified using MiniElute Gel Extraction Kit (Qiagen) or Sephadex™-purified (GE Healthcare Biosciences AB; Uppsala, Sweden) and sequenced with 3100 or 3730 Genetic Analyzer (ABI Biosystems) or by GeneWiz (New Brunswick, N.J.). All samples were sequenced in addition to allele-specific PCR.

Human subjects. Subjects for the study were recruited from the greater New York City area. To control for inter-test variation, all subjects completed the same protocol on two different visits that were four or more days apart. Exclusion criteria for subjects were: allergies to odors or fragrances, a history of nasal illness, upper respiratory infection, seasonal allergy, prior endoscopic surgery on the nose, pre-existing medical condition that has caused a reduced sense of smell such as head injury, cancer therapy, radiation to head and neck, or alcoholism, and pregnancy. Data on the demographics, habits, and usage of the subjects was collected with a computer-administered questionnaire. Demographic questions were largely based on standard US Census questions. During the experiments conducted during the course of the development of embodiments of the present invention (see, e.g., FIGS. 1-3), the genotype of the subjects was unknown. The genotype of the subjects was known during the experiments shown in FIGS. 4 and 5, but the subjects and the test administrators were blind to subject genotype information. 100/255 subjects with the RT/RT genotype and all subjects with other genotypes were invited back for thresholding to androstenone and androstadienone. Not all invited subjects participated in androstenone and androstadienone thresholding. All subjects participating in this thresholding previously participated in the intensity and valence ratings and the assigning of descriptors to odors. Evaluable data from 412 subjects was obtained, who had to meet the minimum criteria of qualifying for the study, completing two study sessions, and providing a blood sample of adequate size for DNA isolation. Subjects whose blood sample subsequently failed to yield adequate quantities of DNA were excluded. The yield of evaluable subjects represented about 77% of all subjects who enrolled in the study, with most subjects being excluded for failing to complete two visits. The numbers of subjects with different OR7D4 genotypes were:

| OR7D4 genotype | # Subjects |
|---|---|
| RT/RT | 255 |
| RT/WM | 100 |
| RT/P79L | 30 |
| WM/WM | 10 |
| RT/S84N | 7 |
| WM/P79L | 4 |
| RT/D52G | 2 |
| WM/S84N | 2 |
| WM/L162P | 1 |
| S84N/P79L | 1 |
| | 412 |

Stimuli for olfactory psychophysics. All odors were presented as one ml of an odor dilution in either propylene glycol or paraffin oil in 20 ml amber glass vials. The concentrations used in the intensity and valence rating are shown in Table 4. All of these compounds were used in the intensity and valence rating portion of the smell test.

TABLE 4

Odors used during experiments of the present invention

| ODOR | LOW CONCENTRATION | HIGH CONCENTRATION | SOLVENT | CAS # |
|---|---|---|---|---|
| (−)-menthol | 1/400 | 1/40 | propylene glycol | 22-18-51-5 |
| (+)-menthol | 1/400 | 1/40 | propylene glycol | 15356-50-2 |
| 1-butane | 1/10,000 | 1/1,000 | paraffin oil | 71-36-3 |
| 2-butanone | 1/10,000 | 1/5,000 | paraffin oil | 78-93-3 |
| 2-decenal | 1/10,000 | 1/1,000 | paraffin oil | 3813-71-1 |
| 2-ethylfenchol | 1/1000,000 | 1/2,000 | paraffin oil | 78368-83-7 |
| 2-methoxy-4-methylphenol | 1/1000,000 | 1/100,000 | paraffin oil | 83-53-6 |
| 4-methylualeric acid | 1/5000,000 | 1/10,000 | paraffin oil | 646-07-3 |
| ambrette | 1/1000,000 | 1/1,000 | paraffin oil | 6015-62-1 |
| androstadienone | 1/100,000 | 1/1,000 | propylene glycol | 794-56-9 |
| androstanone | 1/100,000 | 1/1,000 | propylene glycol | 18339-16-7 |
| anise | 1/50,000 | 1/5,000 | paraffin oil | 8007-70-3 |
| banana | 1/250,000 | 1/10,000 | paraffin oil | |
| bourgeonal | 1/2,000 | 1/200 | paraffin oil | 18127-01-0 |
| buty E acetate | 1/1,000,000 | 1/1,000 | paraffin oil | 123-86-4 |
| butyric acid | 1/1,000,000 | 1/250,000 | paraffin oil | 107-92-5 |
| caproic acid | 1/1,000,000 | 1/2,000 | paraffin oil | 142-61-1 |
| cedarwood | 1/5,000 | 1/3,000 | paraffin oil | 68990-83-0 |
| cineole | 1/100,000 | 1/10,000 | paraffin oil | 470-82-6 |
| cinnamon | 1/50,000 | 1/10,000 | paraffin oil | 8015-93-6 |
| cis-3-hexen-1-ol | 1/250,000 | 1/100,000 | paraffin oil | 928-96-1 |
| citral | 1/50,000 | 1/5,000 | paraffin oil | 5392-40-5 |
| citronella | 1/250,000 | 1/10,000 | paraffin oil | 8000-29-1 |
| decyl aldehyde | 1/25,000 | 1/5,000 | paraffin oil | 112-31-2 |
| diacetyl | 1/10,000,000 | 1/10,000 | paraffin oil | 431-03-8 |
| diethyl sulfide | 1/2,000,000 | 1/100,000 | paraffin oil | 592-88-1 |
| diphenyl ether | 1/500 | 1/200 | paraffin oil | 101-84-8 |
| ethyl vanillin | 1/1,000 | 1/200 | propylene glycol | 121-32-4 |
| ethylene brassylate | 1/500 | 1/100 | paraffin oil | 105-95-3 |
| eugenol | 1/25,000 | 1/1,000 | paraffin oil | 97-53-0 |
| eugenol acetate | 1000,000 | 1/100 | paraffin oil | 93-28-7 |
| eugenol methyl ether | 1/500 | 1/10 | paraffin oil | 93-15-2 |
| fenchone | 1/25,000 | 1/1,000 | paraffin oil | 7787-20-4 |
| fir | 1/100,000 | 1/10,000 | paraffin oil | 8002-09-3 |
| galaxolide | 1/10 | 1/1,000 | paraffin oil | 1222-05-5 |
| geranyl acetate | 1/10,000 | 1/200 | paraffin oil | 105-87-3 |
| guaiacol | 1/50,000,000 | 1/1,000,000 | paraffin oil | 90-05-1 |
| heptaldehyde | 1/10,000,000 | 1/25,000 | paraffin oil | 111-71-7 |
| heptyl acetate | 1/25,000 | 1/2,000 | paraffin oil | 112-06-1 |
| hexyl butyrate | 1/1,000 | 1/100 | paraffin oil | 2639-63-6 |
| leobornyl acetate | 1/2,000,000 | 1/100 | paraffin oil | 125-12-2 |

TABLE 4-continued

Odors used during experiments of the present invention

| ODOR | LOW CONCENTRATION | HIGH CONCENTRATION | SOLVENT | CAS # |
|---|---|---|---|---|
| laobutyraidehyde | 1/100,000 | 1/1,000 | paraffin oil | 78-84-2 |
| laobutyric acid | 1/10,000 | 1/1,000 | paraffin oil | 78-31-2 |
| laoeugenol | 1/25,000 | 1/2,000 | paraffin oil | 97-54-1 |
| leovaleric acid | 2,000,000 | 1/20,000 | paraffin oil | 503-74-2 |
| jasmine | 1/200,000 | 1/1,000 | paraffin oil | 8022-96-6 |
| lime | 1/2,000,000 | 1/5,000 | paraffin oil | 8008-26-2 |
| linalcl | 1/100,000 | 1/100 | paraffin oil | 78-70-6 |
| methanethiol | 1/50,000,000 | 1/10,000,000 | water | 5188-07-8 |
| methyl aalicylate | 1/25,000 | 1/1,000 | paraffin oil | 119-36-8 |
| nonyl aldehyde | 1/100,000 | 1/5,000 | paraffin oil | 124-19-6 |
| nutmeg | 1/25,000 | 1/1,000 | paraffin oil | 8008-45-5 |
| octyl acetate | 1/100 | 1/200 | paraffin oil | 112-14-1 |
| octyl aldehyde | 1/250,000 | 1/25,000 | paraffin oil | 124-13-0 |
| orange | 1/2,500 | 1/100 | paraffin oil | 8008-57-8 |
| pentadecalactone | 1/2,000 | 1/500 | propylene glycol | 106-02-5 |
| phenyl acetaldehyde | 1/8,000,000 | 1/2,000,000 | paraffin oil | 122-78-1 |
| pyrazine | 1/500 | 1/10 | propylene glycol | 290-37-8 |
| r-caryone | 1/100,000 | 1/1,000 | paraffin oil | 6485-40-1 |
| r-limonene | 1/250 | 1/10 | paraffin oil | 5989-27-5 |
| sandalwood | 1/10,000 | 1/1,000 | paraffin oil | 8006-87-9 |
| spearmint | 1/250,000 | 1/5,000 | paraffin oil | 8008-79-5 |
| terpineol | 1/10,000 | 1/100 | paraffin oil | 98-55-5 |
| terpinyl acetate | 1/1,000 | 1/500 | paraffin oil | 30-26-2 |
| undecanal | 1/10,000 | 1/1,000 | paraffin oil | 112-44-7 |
| vanillin | 1/1,000 | 1/200 | propylene glycol | 121-33-5 |
| paraffin oil | | | | 8012-95-1 |
| propylene glycol | | | | 57-55-6 |

For the descriptors task, the following odors and concentrations were used: propylene glcol (pure), pentadecalactone 1/500, vanillin 1/200, and androstenone 1/10,000. The following odors were used for thresholding: adrostenone and androstadienone. These were tested at an initial concentration of binary dilution 27 (118,388,608) in propylene glycol and moved from there in binary steps. The range of dilutions tested was from binary dilution 27 (1:134,217,728) to binary dilution 6 (1:64). Odor vials used for intensity and valence ratings and the assigning of descriptors to odors were used for 40 sessions and then replaced by a new set. Master stocks of each odor were established at the beginning of the study to avoid intertrial variability in odor concentrations.

Figure 7:
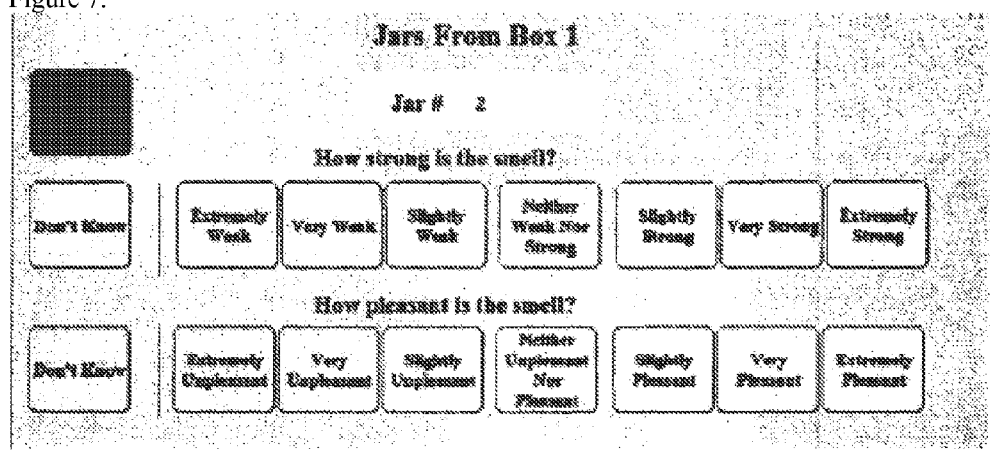
FIG. 7 shows a screenshot from the computerized intensity and valence rating. This is the screen the subjects see after scanning in vial #2 in the intensity and valence rating portion of the smell test. Subjects were instructed to click the "I Can't Smell Anything" if they can't perceive any odor. If subjects are able to perceive the odor, they must rate the strength and valence of the odor. After both selections are made, subjects are prompted to scan vial #3 on the next screen.

Procedures for olfactory psychophysics. All testing was performed in a well-ventilated room. On the first visit, basic vital signs were collected from each subject and an 8.5 cc venous blood sample was collected. All women of child-bearing age took a urine pregnancy test to confirm that they were not pregnant. Smell tests were self-administered and computerized using custom-written applications in FilemakerPro and Microsoft Access. The average subject took 2.5 hours for the sessions that included the rating and descriptor data shown here and 30 minutes for the sessions in which the thresholds were determined. A screenshot from the computerized intensity and valence rating is shown in FIG. 7. This application as well as the application in which odor descriptors are assigned to odors was written in Filemaker Pro. To prevent odor sampling errors, subjects scanned the vial containing the stimulus before being able to rate the stimulus. They were only allowed to proceed with the experiment if the correct vial was scanned. The application for the thresholding was written in Microsoft Access. The computer application for the intensity and valence rating had a built-in mandatory 15 seconds interstimulus interval. However, it took most subjects much longer to move from one stimulus to the next so that it was rarely enforced.

Olfactory ratings. The intensity and valence of 66 odors were rated at two different concentrations (high and low) and the intensity and valence of the two solvents (paraffin oil and propylene glycol) was rated three times. Prior to these ratings, six stimuli that represented the spectrum of intensity and valence of the stimuli used in the study were presented to allow the subjects to calibrate the usage of the scale. The subjects were unaware that the six first stimuli served that purpose. After the rating of the 66 odors at two concentrations and the rating of the solvents, 15 stimuli that were presented earlier in the experiment were repeated to test for the effect of adaptation and olfactory fatigue on the ratings. The subjects were not aware that the last 15 stimuli served this purpose. These 15 stimuli and the six first stimuli were not included in the analysis presented here. The stimuli were presented in the same order in all sessions to not introduce a bias caused by adaptation and olfactory fatigue and to make the measurements between different sessions as comparable as possible. The 15 control stimuli and their concentrations were as follows:

1. guaiacol (high)
2. octyl acetate (high)
3. undecanal (high)
4. paraffin oil
5. heptyl acetate (low)
6. hexyl butyrate (low)
7. butyric acid (high)
8. hexyl butyrate (high)
9. decyl aldehyde (high)
10. 2-decenal (low)
11. cis-3-hexenal (low)
12. nonyl aldehyde (high)
13. 2-methoxy-4-methylphenol (low)
14. decyl aldehyde (low)
15. propylene glycol Although there was variability between the first and second presentation of these stimuli, there was no indication for a systematic difference between the intensity rating at the beginning and end of the session. Eight of the 15 stimuli were rated on average as more intense at the end of the session, whereas seven were rated as less intense. A seven point scale was used to rate intensity and valence with these choices:
Intensity Rating
Extremely Weak
Very Weak
Slightly Weak
Neither Weak nor Strong
Slightly Strong
Very Strong
Extremely Strong
Valence Rating
Extremely Unpleasant
Very Unpleasant
Slightly Unpleasant
Neither Unpleasant nor Pleasant
Slightly Pleasant
Very Pleasant
Extremely Pleasant In addition there was a button on the screen labeled "I can't smell anything" and a button labeled "Don't Know". If the "Don't Know" button was pressed, no rating was recorded. If the "I can't smell anything" button was pressed, a 0 was recorded for the intensity rating and no rating was recorded for the valence rating. The other ratings were transformed according to the following scheme:
Intensity Rating
Extremely Weak=1
Very Weak=2
Slightly Weak=3
Neither Weak nor Strong=4
Slightly Strong=5
Very Strong=6
Extremely Strong=7
Valence Rating
Extremely Unpleasant=1
Very Unpleasant=2
Slightly Unpleasant=3
Neither Unpleasant nor Pleasant=4
Slightly Pleasant=5
Very Pleasant=6
Extremely Pleasant=7

Averages for the ratings of the different genotypes were calculated. Prior to the study the concentrations used for each odorant were determined in intensity matching experiments in which control subjects rated the intensity of stimuli. Odors were considered "low" intensity when the intensity rating was within one standard deviation of the rating for a 1:10,000 dilution of 1-butanol. Odors were considered "high" intensity when the intensity rating was within one standard deviation of a 1:1,000 dilution of 1-butanol. For ethylene brassylate, eugenol methyl ether, (−)-menthol, (+)-menthol, and vanillin the pure odor or the saturated dilution was rated less intense than the criteria for "high" intensity and these odors were therefore presented at the highest possible concentration. Androstenone and andmstadienone could not be intensity matched because of the high variability in the responses across subjects. Ten subjects participated in the intensity matching and six visits were necessary to match all stimuli. The subjects were aware of the purpose of the intensity matching and were instructed to focus on the intensity of the stimulus and disregard the valence. The stimuli used for the intensity and valence rating are shown in Table 4.

Assigning descriptors to odors. Subjects assessed the quality of six odors using an odor profiling method that has shown to produce stable profiles of odorants. Subjects rated 146 odor descriptors (for example: fishy, fruity, tar) on a scale from 0 to 5 with 0 being the default. Odor profiling typically took five minutes per odorant and was performed as a computer-controlled selftest in which the subject's responses were directly recorded. This has the benefit that each subject could work at his or her own pace. Large posters listing all 146 odor descriptors were provided so that subjects could study these before beginning this part of the test. Of the six odors the first (spearmint) was meant to allow the subject to become familiar with the procedure and the descriptors and was not included in the analysis. The descriptors used to describe the other four odors (vanillin, pentadecalactone, androstenone, and propylene glycol) were evaluated. In FIG. 4c the four descriptors that are used in more than 10% of the sessions and that show statistically significant differences between the genotypes are shown. 19/146 descriptors were used in more than 100% of the sessions to describe pentadecalactone, 11/146 for propylene glycol, 23/146 for vanillin, and 21/146 for androstenone (sweet, fragrant, aromatic, musky, bitter, stale, sweaty, light, heavy, rotten fruit, sickening, rancid, putrid foul, vanilla, dirty linen, urine, sharp pungent, ammonia, chemical, cleaning fluid, musty). Of these 74 descriptors, only the four shown in FIG. 4c showed statistically significant differences between the genotypes. In FIG. 4c the percentage with which a given descriptor was used by subjects of a given genotype is plotted.

Threasholding. Detection thresholds (FIG. 3c and FIG. 5b-c) were determined using the "Single Staircase Threshold Detection Method" (see, e.g., Buck, L., et al., Cell 65, 175-187 (1991); Menashe, I., et al., Nat Genet. 34, 143-144 (2003); each of which are herein incorporated by reference in their entireties). This method produced very accurate data on the threshold concentration of a given dour and was easy to administer and for the subjects to perform. The thresholds for each subject on two occasions was tested at least four days apart. This helped to control for inter-trial variability in olfactory performance. The average difference between the thresholds determined on the two days was three binary dilution steps for andmstenone and five for androstadienone.

Figure 8:
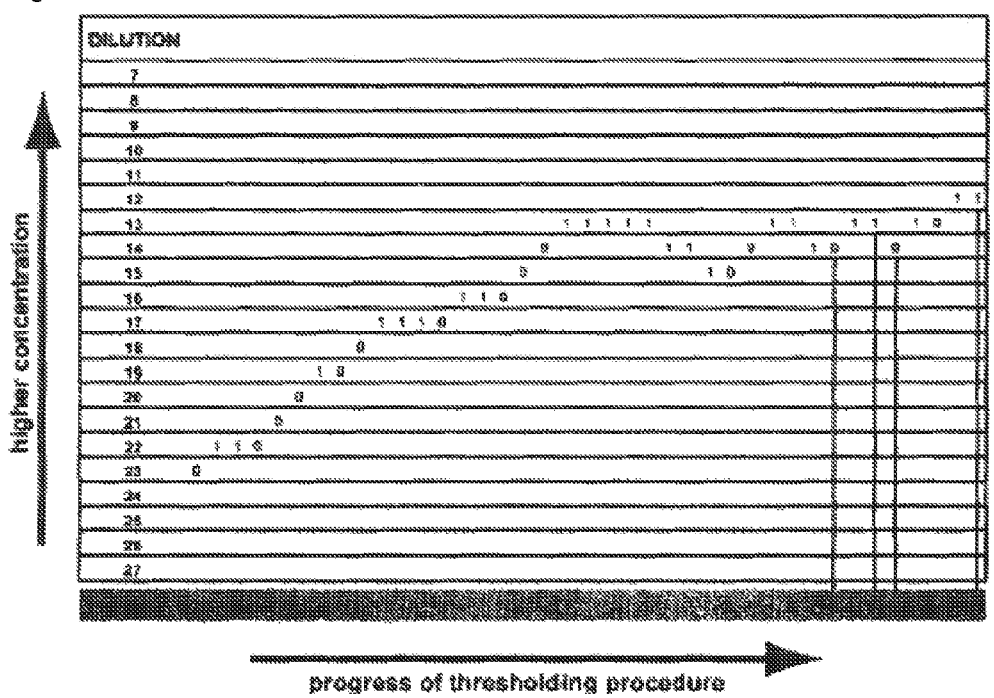
FIG. 8 shows an example of the threshold detection procedure. Detection thresholds were determined using the "Single Staircase Threshold Detection Method" with a computer-controlled thresholding algorithm. Subjects were instructed to sniff two vials, one containing the solvent, the other a dilution of the odorant. All vials were marked with a bar code on the side of the vial and a number on the top of the vial, but contained no other identifying marks. Subjects scanned the bar code of the vial with the stronger odor. If subjects chose the odor vial correctly, they were next prompted to test the next lower concentration of the odor. If subjects chose the solvent vial, they were next prompted with a higher concentration of the odor. As an example of how this algorithm worked, a representative data from a single subject above is presented. In the representation, when the subject scanned the vial containing the odor, this was denoted with a red "1". When the subject scanned the vial containing the solvent this was denoted with a red "0". The thresholding procedure started at dilution 23. Whenever the subject chose the solvent vial, the next higher concentration was tested until dilution 13, where the subject chose the odor vial five times in a row. This was considered the first reversal. Lower concentrations were then tested and the subject was prompted to choose among more dilute odors until two correct odor vial choices were made for one concentration. Note that this subject made an error at dilution 15 and the computer then moved to a higher concentration. This was the second reversal. After this the direction of the change in concentration was reversed. The experiment continued until the seventh reversal at dilution 12. The thresholds reported were the average of the last four reversals. In this example the last four reversals were at dilutions 12, 14, 13, and 14, the threshold for this session was therefore computed to be 13.25.

A custom computer-controlled thresholding test was administered as a self-test to each subject. Briefly, subjects were instructed to sniff two vials, one containing the solvent, the other a dilution of the odorant. Both vials have barcode labels and the procedure was done at a computer equipped with a scanner. Subjects are asked to scan the vial with the stronger odor. Depending on their answer, the procedure was repeated at an adjusted concentration. The total time to determine the threshold varied between subjects but was typically between 15 and 25 minutes per odorant. The thresholding procedure was started at binary dilution 23 for the conventional odors and binary dilution 27 for the steroidal odors. If the subject failed to identify the right vial, the computer prompted the subject to move to a higher concentration in binary dilution steps. This continued until the subject chose the correct vial at one concentration five times in a row. Then the diction of the change in concentration was reversed and a lower concentration was tested. After this first reversal the direction of the change in concentration was reversed whenever on the way down a mistake was made or, on the way up, two right choices were made at one concentration. The experiment continued until the seventh reversal. The thresholds reported were the average of the last four reversals. The data in FIGS. 3 and 5 show the distribution of the thresholds for different genotypes in histograms. Each subject's threshold was the average of two replicates of the experiments on two days four or more days apart. An example of a threshold procedure is shown in FIG. 8.

All publications and patents mentioned in the above specification are herein incorporated by reference. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method for identifying compounds capable of altering OR7D4 activity, comprising:
   a) providing:
      i) a cell comprising an odorant receptor, wherein said odorant receptor is a human OR7D4 polypeptide, wherein said human OR7D4 polypeptide is, in reference to human wild type OR7D4, selected from the group consisting of OR7D4 WM, OR7D4 P79L, OR7D4 D52G, OR7D4 S75C, OR7D4 M136I, OR7D4 L162P, OR7D4 A279D, and OR7D4 L292M, OR7D4 H131Q, and OR7D4 C139Y;
      ii) at least one test compound;
   b) exposing said test compound to said cell
   c) measuring the activity of said human OR7D4 polypeptide; and
   d) identifying said test compound as capable of altering OR7D4 activity based upon said measuring.

2. The method of claim 1, wherein said altering OR7D4 activity comprises inhibiting OR7D4 activity.

3. The method of claim 1, wherein said altering OR7D4 activity comprises enhancing OR7D4 activity.

4. The method of claim 1, wherein said altering OR7D4 activity comprises altering the ability to smell androstenone.

5. The method of claim 4, wherein said altering the ability to smell androstenone comprises an enhanced ability to smell androstenone.

6. The method of claim 4, wherein said altering the ability to smell androstenone comprises a diminished ability to smell androstenone.

7. The method of claim 1, wherein said altering OR7D4 activity comprises altering the ability to smell androstadienone.

8. The method of claim 7, wherein said altering the ability to smell androstadienone comprises an enhanced ability to smell androstadienone.

9. The method of claim 7, wherein said altering the ability to smell androstadienone comprises a diminished ability to smell androstadienone.

10. The method of claim 1, wherein said detecting comprises detecting a reporting agent.

11. The method of claim 1, wherein said test compound is an odiferous molecule.

* * * * *

```
                         SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
ctagtgagca tccaggcac                                              19

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
caggggttca tgatgaccg                                              19

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
ctagtgagca tccaggcat                                              19

<210> SEQ ID NO 4
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n is a or c

<400> SEQUENCE: 4
caggggncat gatgacca                                               18

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
aagtgatgac aagctgagct gc                                          22

<210> SEQ ID NO 6
<211> LENGTH: 23
<212> TYPE: DNA
```

-continued

```
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: n is i

<400> SEQUENCE: 6
ccacaacatn tgccttaggg gta                                            23
```